United States Patent [19]
Anderson et al.

[11] Patent Number: 5,759,517
[45] Date of Patent: Jun. 2, 1998

[54] HEMOGLOBINS AS DRUG DELIVERY AGENTS

[75] Inventors: David C. Anderson, San Bruno, Calif.; Antony James Mathews, Louisville, Colo.

[73] Assignee: Somatogen, Inc., Boulder, Colo.

[21] Appl. No.: 457,753

[22] Filed: Jun. 1, 1995

Related U.S. Application Data

[60] Division of Ser. No. 240,711, Jul. 12, 1994, which is a continuation-in-part of Ser. No. 789,177, Nov. 8, 1991, abandoned, and a continuation-in-part of Ser. No. 789,179, Nov. 8, 1991, Pat. No. 5,545,727.

[51] Int. Cl.$^6$ .......................... A61K 51/00; A61M 36/14
[52] U.S. Cl. ................... 424/1.69; 530/385; 424/1.11; 424/1.65; 424/9.1
[58] Field of Search .......................... 424/1.69, 1.11, 424/1.65, 9.1, 9.3; 530/385; 540/145; 514/6

[56] References Cited

U.S. PATENT DOCUMENTS

| | | |
|---|---|---|
| 3,934,008 | 1/1976 | Rittel et al. ............... 424/1.11 |
| 3,980,764 | 9/1976 | Adams . |
| 4,001,200 | 1/1977 | Bonsen et al. . |
| 4,001,401 | 1/1977 | Bonsen et al. ............... 424/177 |
| 4,042,677 | 8/1977 | Molinski et al. . |
| 4,053,590 | 10/1977 | Bonsen et al. . |
| 4,061,736 | 12/1977 | Morris et al. ............... 424/177 |
| 4,291,013 | 9/1981 | Wahlig et al. . |
| 4,301,144 | 11/1981 | Iwashita et al. . |
| 4,321,259 | 3/1982 | Nicolau et al. . |
| 4,336,248 | 6/1982 | Bonhard et al. . |
| 4,338,397 | 7/1982 | Gilbert et al. . |
| 4,374,932 | 2/1983 | Pitzele et al. . |
| 4,377,512 | 3/1983 | Ajisaka et al. . |
| 4,412,989 | 11/1983 | Iwashita et al. . |
| 4,473,476 | 9/1984 | Scannon ............... 424/101 |
| 4,473,563 | 9/1984 | Nicolau et al. . |
| 4,474,893 | 10/1984 | Reading . |
| 4,497,932 | 2/1985 | Trovati . |
| 4,500,507 | 2/1985 | Wong ............... 424/1.11 |
| 4,511,503 | 4/1985 | Olson et al. . |
| 4,512,922 | 4/1985 | Jones et al. . |
| 4,529,719 | 7/1985 | Tye ............... 514/6 |
| 4,540,564 | 9/1985 | Bodor . |
| 4,551,433 | 11/1985 | DeBoer . |
| 4,584,130 | 4/1986 | Bucci et al. ............... 514/6 |
| 4,598,064 | 7/1986 | Walder . |
| 4,599,197 | 7/1986 | Wetzel . |
| 4,600,531 | 7/1986 | Ivalder ............... 530/385 |
| 4,620,948 | 11/1986 | Builder et al. . |
| 4,650,786 | 3/1987 | Wong . |
| 4,670,417 | 6/1987 | Iwasaki et al. . |
| 4,704,692 | 11/1987 | Ladner . |
| 4,710,488 | 12/1987 | Wong . |
| 4,730,936 | 3/1988 | Thorjmsen, Jr. . |
| 4,738,952 | 4/1988 | Ecanow et al. . |
| 4,769,326 | 9/1988 | Ruter . |
| 4,774,180 | 9/1988 | Toth et al. . |
| 4,777,244 | 10/1988 | Bonhard et al. . |
| 4,783,529 | 11/1988 | Lavallee et al. ............... 424/1.11 |
| 4,839,419 | 6/1989 | Kramer et al. . |
| 4,840,896 | 6/1989 | Reddy et al. ............... 435/68 |
| 4,842,856 | 6/1989 | Hoederath et al. . |
| 4,849,142 | 7/1989 | Fujioka et al. . |
| 4,868,158 | 9/1989 | Masquelier et al. . |
| 4,879,272 | 11/1989 | Shimoda et al. . |
| 4,918,008 | 4/1990 | Gauri . |
| 4,920,194 | 4/1990 | Feller et al. . |
| 5,028,588 | 7/1991 | Hoffman et al. ............... 514/6 |
| 5,049,493 | 9/1991 | Khosla et al. ............... 435/69.6 |
| 5,069,936 | 12/1991 | Yen ............... 424/1.11 |
| 5,173,426 | 12/1992 | Fischer et al. ............... 435/69.6 |
| 5,234,903 | 8/1993 | Nho et al. ............... 514/6 |
| 5,250,665 | 10/1993 | Kluger et al. ............... 530/385 |
| 5,545,727 | 8/1996 | Hoffman et al. ............... 536/234 |
| 5,599,907 | 2/1997 | Anderson et al. ............... 530/385 |

FOREIGN PATENT DOCUMENTS

| | | |
|---|---|---|
| 117058 | 8/1984 | European Pat. Off. . |
| 161937 | 11/1985 | European Pat. Off. . |
| 206448 | 12/1986 | European Pat. Off. . |
| 319206 | 6/1989 | European Pat. Off. . |
| 0337799 | 10/1989 | European Pat. Off. . |
| 361720 | 4/1990 | European Pat. Off. . |
| 0396387 | 11/1990 | European Pat. Off. . |
| 0413622 | 2/1991 | European Pat. Off. . |
| 3938953 | 11/1989 | Germany . |
| 1261398 | 10/1989 | Japan . |
| 3123799 | 5/1991 | Japan . |
| 8711614 | 5/1987 | United Kingdom . |
| 8600527 | 1/1986 | WIPO . |
| 8601409 | 3/1986 | WIPO . |
| WO8601409 | 3/1986 | WIPO . |
| 8702061 | 4/1987 | WIPO . |
| WO8707832 | 12/1987 | WIPO . |
| 8806601 | 9/1988 | WIPO . |
| 8809179 | 12/1988 | WIPO . |
| 9000609 | 1/1990 | WIPO . |
| 9013645 | 11/1990 | WIPO . |
| WO9013309 | 11/1990 | WIPO . |
| 9108220 | 6/1991 | WIPO . |
| 9109134 | 6/1991 | WIPO . |
| 9308842 | 5/1993 | WIPO . |

OTHER PUBLICATIONS

Perutz et al (1986), J. Am. Chem. Soc, vol. 108, pp. 1064–1010, "Hemoglobin as a Receptor of Drugs and Peptides: X-ray Studies of the Stereochemistry of Binding".
Mathews et al (1989), J. Biol. Chem., vol. 264, No. 28, pp. 16573–16583, "The Effects of E7 and E11 Mutations on the Kinetics of Ligand Binding to R State Human Hemoglobin".

(List continued on next page.)

*Primary Examiner*—John Kight
*Assistant Examiner*—Dameron Jones
*Attorney, Agent, or Firm*—Iver P. Cooper

[57] ABSTRACT

A tracer, such as a radioisotope, is conjugated to a hemoglobin-like protein, such as normal hemoglobin, for use as an in vitro diagnostic imaging agent.

18 Claims, No Drawings

OTHER PUBLICATIONS

Taylor et al (1992), J. Nucl. Med., vol. 33, pp. 1836–1842, Technetium–99m–N1–(2–mercapto–2–methyl propyl)–N2–(2–proparcylthio–2–methyl–propyl)–1,2–benzene didmine ($T_{691}$) : Preclinical Studies of a Potential New Tracer of Regional Cerebral Perfusion.

Nagai et al, "Refolding and Crystallographic Studies . . ." Biochem. Soc. Trans. 16 (2): 108–110, 1988.

Moens et al, "A Structural Domain of the Covalent Polymer Cali . . ." J. Biol. Chem. 263: 4679–4685, Apr. 5, 1988.

Shen, "Multiple joined genes prevent product degradation . . . E. coli", PNAS 81:4627–4631, Aug. 1984.

Schulz et al, "Increased Expression in E. coli of a Synthetic Gene " J. Bacteriology 169 (12): 5385–5392, Dec. 1987.

Liebhater et al., PNAS 77: 7054–7058, Dec. 1950.

Nagai et al., PNAS 82: 7252–7255, Nov. 1985.

Saito et al. J. Biochem. 101: 1281–1288, 1987.

Schoner, et al., PNAS 83: 8506–8510, Nov. 1986.

Springer et al., PNAS 84: 8961–8965, Dec. 1987.

Hallewell et al., J. Biol. Chem. 264: 5260–5268, Mar. 1989.

Guareute et al., PNAS 79: 7410–7414, Dec. 1982.

DeLaach et al, Am. J. Vel. Res., vol. 42, No. 4, pp. 667–669, Apr. 1981.

Chen et al, Journal of Controlled Release, vol. 8, pp. 93–101, 1988.

Willmott et al, Journal of Controlled Release, vol. 8, pp. 103–109, 1988.

Mathews et al, The Journal of Biological Chemistry, vol. 264, No. 28, pp. 16573–16583, Oct. 5, 1959.

Perutz et al., J. Am. Chem. Soc., vol. 108, pp. 1064–1078, 1986.

Peru et al, J. Am. Chem. Soc. 1078, 1986, vol. 108.

Abstract DBA Accession No. 89–12842 on Dialog File 357, of DeBaeteller, et al.; Yeast as a source of human lysozyme–synthetic gene cloning and expression in S. cerevisiae, Hedec. Fac. Landbouwet. Rijksuniv. Gent, 53:2135–41 (1988).

DeBoer et al.; Portable Shine–Delgarno Regions: A System for a Systematic Study of Defined Alterations of Nucleotide Sequences within E. coli Ribosome Binding Sites; DNA, 2:231–235 (1983).

DeGrado et al.; Protein Design, a Minimalist Approach Science 243:622 (1989).

Denefle et al.; Chemical synthesis of a gene coding for human angiogenin, its expression in E. coli and conversion of the product into its active form; Gene, 56:61–70 (1987).

DeVenuto, et al.; Appraisal of Hemoglobin Solution as a Blood Substitute Surgery, Gynecology and Obstetrics, 149:417–436 (1979).

Dickerson et al.; Evolution of the Oxygen Carriers Hemoglobin, Structure, Function, Evolution and Pathology; Chapter 3:66–115 (1983).

DiMarchi et al.; Chemical synthesis of human epidermal growth factor (EGF) and human type α transforming growth factor (TGFα); Peptides:Chemistry and Biology, 202–203 (1988).

Dowling et al.; A Clinical Study of Fluosol and Hyperbaric Oxygen as an Adjunct to Radiation Therapy Biomat. Art Cells and Immobil. Biotech. Abstract 19:377 (1991).

Ebert et al.; On the Introduction of Disulfide Crosslinks into Fibrous Proteins and Bovine Serum Albumin Adv. Exp. Med. Biol. 86A:235–245 (1977).

Edens et al.; Synthesis and Processing of the Plant Protein Thaumatin in Yeast Cell, 37:629–633 (1984).

Ernst, J.F.; Improved Secretion of Heterologus Proteins by S. cerevisiae: Effects of Promoter Substitution in Alpha–Factor Fusions; DNA 5(6):483–491 (1986).

Feola et al.; Nnephrotoxicity of Hemoglobin Solutions Biomat. Art. Cells Art. Org. 18(2)233–249 (1990).

Fermi et al.; The Crystal Structure of Human Deoxyhaemoglobin at 1–74 A Resolution J. Mol. Biol.; 175:159–174 (1984).

Freedman et al.; Formation of Disulphide bonds Biological Laboratory, University of Kend, Canterbury, U.K.; 158–212 (1980).

Fronticelli et al.; Bovine hemoglobin pseudo–crosslinked with mono( 3,5–dibromosalicyl)–fumarate Eur. J. Biochem. 192:331–336 (1990).

Fushitani et al.; The Amino Acid Sequences of Chains a, b, and c That Form the Trimer Subunit of the Extracellular Hemoglobin from Lumbricus terrestris; J. Biol. Chem.; 263(14):6502–6517 (1988).

Fushitani et al.; The Extracellular Hemoglobin of the Earthworm, lumbnicus terrestrisJ. Biol. Chem.; 266(16):10275–10251 (1991).

Gatenby et al.; Co–expression of both the maize large and wheat small subunit genes ribulose–biphosphate carboxylase in E. coli; Eur. J. Biochem; 168:227–231 (1987).

Giatini et al.; Reovirus major capsid protein expressed in Escherichia coli Gene, 56:153–160 (1987).

Gitelson, et al.; Two–stage thermal unfolding of [Cys[55]]–substituted Cro repressor of bacteriophage lambda FEBS Lett., 289(2):201–204 (1991).

Goossens, et al.; Triplicate alpha globin loci in humans: PNAS, 77(1):518–521 (1980).

Gottesman et al.; Transcription Antitermination by Bacteriophage Lambda N Gene Product J. Mol. Biol. 140:57–75 (1980).

Gould et al.; The Development of Polymerized Pyridoxylated Hemoglobin Solution as a Red Cell Structure Ann. Emerg. Med., 15:1416–1419 (1986).

Greaves et al.; A transgenic mouse model of sickle cell disorder Nature, 343:183–185 (1990).

Greer et al.; Three Dimensional Structure of Hemoglobin Rainier Nature New Biology, 230:261–264 (1971).

Guthrie et al.; The Molecular Biology of the Yeast Sacharomyces 487–528 (Cold Spring Harbor Laboratory; 1988).

Haase–Pettingell and King; Formation of Aggregates from a Thermolabile in vivo Folding Intermediate in P22 Talispike Maturation; J. Biol. Chem., 263:4977–83 (1988).

Hallewell et al.; Amino Terminal Acetylation of Authentic Human CuZn Superoxide Dismutase Produced in Yeast Biotechnology, 5:363–366 (1987).

Hanahan, Douglas; Studies on Transformation of Escherichia coli with Plasmids J. Mol. Biol., 166:557–580 (1983).

Hanscombe, et al.; High–level, erythroid–specific expression of the human alpha globin gene in transgenic mice and the production of human hemoglobin in murine erythrocytes; Genes and Dev., 3:1572–81 (1989).

Harley et al.; Analysis of E. coli Promoter Sequences Nucleic Acids Research, 15(5):2343–61 (1987).

Hayashi et al.; Haemoglobin Rainier; β145 (HC2) Tyrosine—Cysteine and Haemoglobin Bethesda: β145 (HC2) Tyrosine—Histidine; Nature New Biology, 230:264–67 (1971).

Herman et al.; Enhancement of Radiation Therapy by an Experimental Concentrated Perfluorooctylbromide (Oxygent) Emulsion in the Lewis Lung Carcinoma: Biomat. Art. Cells and Immobil. Biotech. Abstract 19:395:1991.

Herskovits et al.; The Hemoglobin of the Aquatic Snail, Planorbella Dury (Wetherby) Comp. Bioche. Physiol., 95b(2):321–326 (1990).

Hoffman et al.; Expression of fully functional tetrameric human hemoglobin in *E. coli* Proc. Natl. Acad. Sci., 87:8521–8525 (1990).

Holden et al.; Effect of a PFOB Emulsion (Oxygent) and Carbogen Breathing on the Tumor Cell Survival of the FSaiiC Fibrosarcoma After Treatment with Antitumor Alkylating Agents; Biomat. Art. Cells and Immbil. Biotech. Abstracts 19:399 (1991).

Holland et al.; Homolgous Nucleotide Sequences at the 5' Termini of Messenger RHAs Synthesized from the Yeast Enolase and Glyceraldehyde–3–phosphate Dehydrogenese Gene Families; J. Biol. Chem., 258:5291–5299 (1983).

Holland et al.; The Primary Structure of Two Yeast Enolase Genes J. Biol. Chem. 256:1385–1395 (1981).

Honig et al.; Hemoglobin Nigeria (α–‖Ser →Cys): A New Variant Associated with α–Thalassemia Blood, 55:131–137 (1980).

Horwitz et al.; Secretion of Functional antibody and Fab fragment from yeast cells Proc. Natl. Acad. Sci., 85:8678–8682 (1988).

Hui et al.; Mutagenesis of the three bases preceding the start codon of the β–galactosidase mRNA and its effect on translation in *E. coli*; EMBO J., 3(3):623–629 (1984).

Hui et al.; Specialized ribosome system: Preferential translation of a single mRNA species by a subpopulation of mutated ribosomes in *E. coli*; Proc. Natl. Acad. Sci., 84:4762–4766 (1987).

Ishimoto et al.; A Variant Hemoglobin found in *Hacaca fuscata*: Another Polymerizing Hemoglobin of Hacaques J. Anthrop. Soc. Nippon, 83(3):233–243 (1975).

Ito et al.; Transformation of Intact Yeast Cells Treated with Alkali Cations J. Bacteriol., 153(1):163–168 (1983).

Johnston et al.; Sequence That Regulate the Divergent GAL1–GAL10 Promoer in *S. cerevisiae* Mol. Cell. Biol., 4:1440–1448 (1984).

Kastelein et al.; Effect of the sequences upstream from the ribosome–binding site on the yield of protein from the cloned gene for phge MS2 coat protein; Gene, 23:245–54 (1983).

Kavanaugh et al.; Affinity Labeling of Hemoglobin with 4,4'–Diisothiocyanostilbene–2,2'–disulfonate: Covalent cross–linking in the 2,3–diphosphoglycerate binding site; Biochemistry, 27:1804–1808 (1988).

Keipert et al.; Preparation of in Vitro Characteristics of a Blood Substituted based on pyridoxylated polyhemoglobin; Appl. Biochem. Biotechnol., 10:133–131 (1984).

Keipert et al.; Pyridoxylated–polyhemoglobin solution: A low viscosity oxygen–delivering blood replacement fluid with normal oncotic pressure and long–term storage feasibility; Biomat. Art. Cell. Art. Org., 16(–3):185–196 (1988).

King et al.; Recovery of recombinant proteins from yeast Biochem Soc. Transac., 16:1083–1086 (1988).

Kitano et al.; Recombinant Hepatitis B Virus Surface Antigen P31 Accumulates as Particle in *S. cerevisiae* Biotechnology, 5:281–283 (1987).

Konigsberg et al.; Evidence for use of rare codons in the dnaG gene and other regulatory genes of *E. coli* Proc. Natl. Acad. Sci., 80:687–91 (1983).

Kozak, Marilyn; Point Mutations Define a Sequence Flanking the AUG Initiator Codon That Modulates Translation by Eukaryotic Ribosomes; Cell, 44:263–292 (1986).

Krueger et al.; Protein Inclusion Body Formation and Purification Biopharm, 40–45 (Mar. 1989).

Laemmli, U.K.; Cleavage of Structural Proteins during the Assembly of the Head of Bacteriophage T4 Nature, 227:680–685 (1970).

Langley et al.; Recombinant–DNA–derived bovine growth hormone from *E. coli* Eur. J. Biochem., 163:313–321 (1987).

Lau et al.; Amplification and expression of human α–globin genes in Chinese hamster ovary cells Biols Abs. 79(1):3755 (1984).

Lawn et al.; The Nucleotide Sequence of the Human Beta–Globin Gene Cell, 21:647–651 (1980).

Lee et al.; Cloning with tandem gene systems for high level gene expression Nucleic Acids Research 12:6797 (1984).

Lee et al.; Ultrapure, Stroma–Free, Polymerized Bovine Hemoglobin Solution: Evaluation of Renal Toxicity J. Surgical Research, 47:407–411 (1989).

Lee et al.; Modulation of Expression of the Human Gamma Interferon Gene in *E. coli* by site–directed mutagenesis; Bioche. Biophys. Res. Comm. 151(1):598–607 (1988).

Long et al.; Pharmacologic and metabolic determinants in swine receiving PFOB emulsion i therapy of severe anemia; Biomat. Art Cells Immob. Biotech., 19(2):514 (1991).

Long et al.; Effect of Emulsion Concentration on Biodistribution of PFOB in Tumor–Bearing Mice Biomat. Art Cells Immob. Biotech, 19(2):515 (1991).

Long et al.; Cyclooxygenase inhibition with ibuprofen; effect on biodistribution of perfluoroocytylbromide Biomat. Art Cells Immob. Biotech, 19(2):513 (1991).

Lowe et al.; Protective effects onf emulsified perfluorochemicals in experimental photodynamic therapy Biomat. Art Cells Immob. Biotech, 19(2):420 (1991).

Lutz et al.; Combination of Treatment with Perfluorochemicals and free radical scavengers Biomat. Art Cells. Immob. Biotech, 19(2):423 (1991).

Hanning et al.; Evolution of a polymeric globin in the brine shrimp Artemia Nature, 348:653 (1990).

Hanning et al.; Preparation, properties, and plasma retention of human hemoglobin derivatives: Comparison of uncrosslinked carboxymethylated hemoglobin with crosslinked tetrameric hemoglobin; PNAS, 88:3329–3333 (1991).

Harotta et al.; Human Beta–Globin Messenger RNA J. Biol. Chem., 252:5040–5053 (1977).

Matsumura et al.; Control of Enzyme Activity by an Engineered Disulfide Bond Science, 243:792–794 (1989).

Matsumura et al.; Stabilization of pahge T4 lysozyme by engineered disulfide bonds PNAS, 86:6562–6566 (1989).

Matasumura et al.; Substantial increase of protein stability by multiple disulphide bonds Nature 342:291–293 (1989).

McAlister et al.; Differential Expression of the Three Yeast Glyceraldehyde–3–phosphate dehydrogenase genes J. Biol. Chem., 260:15019–15027 (1985).

McCarthy et al.; Translational Initiation frequency of atp genes from *E. coli:* identification of an intercistronic sequence that enhances translation; EMBO J. 4(2):519–526 (1985).

McNally et al.; Coexpression and assembly of myosin heavy chain and myosin light chain in *E. coli* PNAS, 85:7270–7273 (1988).

Meng et al.; Reduction studies on bacterial recombinant somatomedin C insulin–like growth factor–1 J. Chromatogr., 443:183–92 (1988).

Moo–Penn et al.; Hemoglobin presbyterina:beta 108 (G10) asparagine → Lysine: A hemoglobin variant with low oxygen affinity; FEBS Letter, 92(1):53–56 (1978).

Mott et al., Maximizing gene expression from plasmid vectors containing the lambda $P_L$ promoter: Strategies for overproducing transcription termination factor p; PNAS, 82:88–92 (1985).

Murakami et al.; A genetically engineered P450 monooxygenase: Construction of the functional fused enzyme between rat cytochrome P450c and NADPH–cytochrome P450 reductase; DNA, 6:189–97 (1987).

Nagai et al.; Generation of beta–globin by sequence–specific proteolysis of a hybrid protein produced in *E. coli*; Nature, 309:810–812 (1984).

Nagai et al.; Trypsin–catalyzed Synthesis of Peptide Bond in Human Hemoglobin J. Biol. Chem., 257:1622–25 (1982).

Niazl et al.; Hemoglobinopathies due to abnormal functional properties of hemoglobin: Molecule Part 1. Stable abdnormal hemoglobins with high oxygen affinity and erythrocytosis; Kawasaki Med. J. 12(10):1–14 (1986) abst.

Pantoliano et al.; Protein Engineering of Subtilisin BPN': Enhanced Stabilization through the Introduction of two cysteines to form a disulfide bond; Biochemistry, 26:2077–2082 (1987).

Paul et al.; Immunocytochemical demonstration of human proinsulin chimeric polypeptide within cytoplasmic inclusion bodies *E. coli*; Eur. J. Cell Biol., 31:171–174 (1983).

Perry et al., Disulfide Bond Engineered into T4 Lysosyme: Stabilization of the Protein toward thermal inactivation; Science, 226:555–557 (1984).

Peters et al.; A mouse beta–globin mutatnt that is an exact model of hemoglobin rainier in man Genetics, 110:709–721 (1985).

Ranty et al.; An intra–dimeric crosslink of large subunits of spinach ribulose–1,5,–biphosphate carboxylase/oxygenase is formed by oxidation of cysteine 247; Eur. J. Biochem. 200:353–358 (1991).

Richardson et al.; The expression of functional ricin B–chain in *S. cerevisiae* Biochem. Biophys. Acta, 950:384–94 (1988).

Riggs, A.F.; Hemoglobin polymerization in mice Science, 147:621–623 (1965).

Riggs et al.; Polymerization of frog and turtle hemoglobins PNAS, 51:1127–1134 (1964).

Roberts et al.; A general method for maximizing the expression of a cloned gene PNAS, 76(2):760–764 (1979).

Rockwell et al.; Preclinical evaluations of a perfluoroctyl–bromide emulsion as an adjunct to radiotherapy Biomat. Art Cells Immob. Biotech., 19(2):476 (1991).

Saiki et al.; Enzymatic amplification of beta–globin genomic sequences and restriction site analysis for diagnosis of sickle cell anemia; Science, 230:1350–1354 (1985).

Sanger et al.; A rapid method for determining sequences in DNA by primed synthesis with DNA polymerase J. Mol. Biol., 94:441–448 (1975).

Sanger et al.; DNA sequencing with chain–terminating inhibitors PNAS, 74:5463–5467 (1977).

Sauer et al.; An engineered intersubunit disulfide enhances the stability and DNA bindong of the n–terminal domain of lambda repressor; Biochemistry, 25:5992–5998 (1986).

Scannon, Patrick; Molecular modifications of hemoglobin Crit. Care Med., 10(4):261–265 (1982).

Scherer et al.; The ribosome binding site recognized by *E. coli* ribosomes have regions with signal character in both the leader and protein coding segments; Nucleic Acids Research, 8:3895–3907 (1907).

Schulz et al.; Principles of protein structure Springer–Verlag, Table 1–2 (1979).

Semchuk et al.; Synthetic alpha–helical model proteins: Contribution of hydrophobic residues protein stability; Dept. of Biochem. & Med. Res. Council 566–570 (1990) River and Marshall eds.

Shaanan, Boaz; Structure of human oxyhaemoglobin at 2–1 A resolution J. Mol. Biol., 171:31–59 (1983).

Shine et al.; Determinant of cistron specificity in bacterial ribosomes Nature 254:34–39 (1975).

Skerra et al.; Assembly of a functional immunoglobulin in $F_v$ fragment in *E. coli* Science, 240:1038–41 (1988).

Smith et al.; Heterologous protein secretion from yeast Science, 229:1219–1229 (1985).

Snyder et al.; HbXL99α: A hemoglobin derivative that is cross–linked between the α subunits is useful as a blood substitute; PNAS, 84:7280–7284 (1987).

Stamatoyannopoulos et al.; Single chain alkali resistance in hemoglobin rainiers: β145 tyrosine→histidine Science, 166:1005–06 (1969).

Stetler et al., Secretion on active, full–and half length human secretory leukocyte protease inhibitior by *S. cerevisiae*; Biotechnology, 7:55–60 (1989).

Struhl et al.; High–frequency transformation of yeast: Autonomous replication of hybrid DNA molecules PNAS, 75(6):1035–1039 (1979).

Strubbs et al.; Production of pea lectin in *E. coli* J. Biol. Chem., 261:6141–44 (1986).

Suganuma et al.; Elimination of disulfide bonds affects assembly and secretion of the human chorionic gonadotropin β subunit; J. Biol. Chem., 264(32):19302–19307 (1967).

Suzuki et al.; The deep–sea tube worm hemoglobin; Subunit structure and phylogenetic relationship with annelid hemoglobin; Zoological Science, 6:915–926 (1989).

Suzuki et al.; Primary structure of a constituent polypeptide chain (AIII) of the giant haemoglobin from the dee–sea tube worm lamellibrachia; Biochem. J., 266(1):221–226 (1990).

Takenaka et al.; Hemoglobin izu(MACACA): β83 (EF 7) Gly →Cys. A new hemoglobin variant found in the Japanese Monkey (MACA Fuscata); Biochem. Biophys. Acta., 492:433–444 (1977).

Tamet al.; The hemoglobins of the bullfrog *rana catesbeiana* J. Biol. Chem., 261(18):8290–8294 (1986).

Tam et al., Impairment of renal function by stroma–free hemoglobin in rats J. Lab. Clin. Med., 111:189–193 (1988).

Teicher et al.; Effect of a bovine hemoglobin preparation (PBHS) on the response of two . . . agents Biomat. Art. Cells Immob. Biotech. Abstracts 19(2):491 (1991).

Teicher, Beverly; Use of Perfluorochemical emulsions in cancer therapy Biomat. Art. Cells Immob. Biotech.. Abstracts 19(2):490 (1991).

Thim et al.; Secretion of human insulin by a transformed yeast cell FEBS Letter. 212(2):307–312 (1987).

Thornton, J.M.; Disulphide bridges in globular proteins J. Mol. Biol. 151:261–287 (1981).

Tondo et al.; Functional properties of hemoglobin porto alegre ($a2^A\beta_2$ $^{9Ser \to Cys}$) and the Reactivity of its extra cysteinyl residue; Biochim. Biophys. Acta., 342:15–20 (1974).

Tondo, C.V.; Osmometric study of the subunit dissociation of hemoglobin porto alegre (β9(A6)Ser–ΔCys) Dissulfide Polymer; An Acad. bras. Ci., 59(3):243–251 (1987).

Toth et al.; Internal structure of *E. coli* glycyl–tRNA synthetase examined by subunit polypeptide chain fusions; J. Biol. Chem., 261:6643–46 (1986).

Travis et al., Isolation and properties of recombinant DNA produced variants of Human $\alpha_1$–proteinase inhibitor J. Biol. Chem., 260(7):4384–4389 (1985).

Tschumper et al., Sequence of a yeast DNA fragment containing a chromosomal replicator and the TRP1 gene Gene, 10:157–166 (1980).

Tsuji et al., Characterization of disulfide bonds in recombinant proteins: Reduced human interleukin 2 in inclusion bodies and its oxidative refolding; Biochemistry, 26:3129–3134 (1987).

van der plas et al.; Purification and physical characteristics of a hemoglobin solution modified by coupling to 2–nor–2–formylpyridoxal 5'–phosphate (NFPLP); Transfusion, 28(6):525–530 (1988).

Verbakel et al.; Construction of expression plasmids for *S. cerevisiae*: application for synthesis of poliovirus protein VP2; Gene: 61:207–215 (1987).

Villafranca et al.; An engineered disulfide bond in dihydrofolate reductase Biochemistry, 26:2182–2189 (1987).

Wagenbach et al.; Synthesis of wild type and mutant human hemoglobins in *S. cerevisiae* Biotechnology, 8:57–61 (1991).

Weir et al;. Purification and renaturation of recombinant human interleukin–2 Biochem. J., 245:85–91 (1987).

Wells et al.; In vivo formation and stability of engineered disulfide bonds in subtilisin J. Biol. Chem., 261(14):6564–6570 (1986).

White et al.; Effects of crosslinking on the termal stability of hemoglobin Arch. Biochem. Biophys., 258(1):51–57 (1987).

Winterhalter et al.; Preparation, properties, and specific recombination of αβ–globin subunits J. Biol. Chem. 239:3699 (1964).

Yabuki et al.; Characterization of pyridoxalated hemoglobin–polyoxyethylene conjugate as a physiologic oxygen carrier; Transfusion, 30(6):516–520 (1990).

Yang et al.; Thermal stability of hemoglobin crosslinked in the T–state by Bis(3,5–dibromosalicyl) fumarate Bioch. Biophys. Res. Comm., 174(2):519–523 (1991).

Yang et al.; The effect of crosslinking by BIS(3,5–dibromosalicyl) fumarate on the autoxidation of hemoglobin Bioch. Biophys. Res. Comm., 163(2):733–738 (1989).

Yip et al.; Influence of Prosthetic Groups on Protein Folding and Subunit Assembly J. Biol. Chem., 247:7237–44 (1972).

Yip et al.; Reconstitution of native human hemoglobin from separated globin chains and alloplex intermediates PNAS, 74:64–68 (1977).

Yutani et al.; Effect of amino acid substitutions on conformational stability of a protein Adv. Biophys., 20:13–29 (1985).

Zaghloul et al.; Translational coupling in *E. coli* of a heterologous bacillus subtilis *E. coli*gene fusion J. Bacteriol., 168(2):1033–1035 (1986).

Bunn et al.; Hemoglobin:Molecular Genetic and Clinical Aspects (W.B. Saunders Co., Philadelphia, PA; 1986) pp. 15–60, 91–105, 126–222, 381–451, 595–622, 634–662.

Bunn et al.; The renal handling of hemoglobin: I. Glomerular Filtration J. Exp. Med. 129::909–923 (1969).

Bunn et al.; The renal handling of hemoglobin: II. Catabolism J. Exp. Med. 129:925–934 (1969).

Canton et al.; The conformation of biological macromolecules Biophysical Chemistry 266–269 (1980).

Carlson et al.; A new means of inducibly inactivating a cellular protein Mol. Cell. Biology, 8(6):2638–46 (1988).

Charnay et al.; Differences in human alpha and beta–globin gene expression in mouse erythroleukemia cells: The role of intragenic sequences; Cell, 38:251–263 (1984).

Bennetzen et al.; Codon Selection in Yeast J. Biol. Chem., 257:3026–3031 (1982).

Better et al.; *E. coli* secretion of an active chimeric antibody fragment Science, 240:1041–43 (1988).

Birnbolm and Doly; A rapid alkaline procedure for screening recombinant plasmid DNA Nucleic Acids Res., 7:1513–1520 (1979).

Bitter and Egan; Expression of heterogous genes in *S. cerevisiae* from vectors utilizing the glyceraldehyde–3–phosphate dehydrogenase gene promoter; Gene, 32:263–274 (1984).

Blackwell et al.; Hemoglobin Ta–Li:β83 Gly →Cys Biochm. Biophys. Acta, 243:467–474 (1971).

Boel et al.; Expression of human pancreatic polypedtide precursors form a dicistronic mRNA in mammaian cells FEBS Lett, 219:181–189 (1987).

Bonaventura et al.; Hemoglobin Kansas, a human hemoglobin with a neutral amino acid substitution and an abnormal oxygen equilibrium; J. Biol. Chem., 243(5):980–991 (1968).

Bonaventura et al.; Polymerization of hemoglobins of mouse and man:structural basis Science, 149:800–802 (1967).

Botstein et al.; Metabolism and gene expression The Molecular Biology of the Yeast Saccharomyces, Stathern et al. eds. 607–636 (1982)..

Brake, A.J.; Secretion of heterologous proteins directed by the yeast–α–factor leader Yeast Genetic Engineering, 269–280 (1989), Barr et al. eds.

Brosius and Holy; Regulation of ribosomal RNA promoters with a synthetic lac operator PNAS, 81:6929–6933 (1984).

Brouwer, et al.; Carbodiimide–mediated coupling of benzenepentacarboxylate to human hemoglobin; Structural and functional consequences; Biomater. Artif. Cells Artif. Organ. Abstracts, 19(2):361 (1991).

Bucci et al.; Bovine hemoglobin as a basis for artificial oxygen carriers Biomat. Art. Cells, Art. Org., 16(1–3):197–204 (1988).

Chatterjee et al.; Isolation and characterization of a new hemoglobin derivative crosslinked between the α chains (Lysine 99$\alpha_1$—>Lysine 99α2); J. Biol. Chem. 261:9927–37 (1986).

Chou et al.; Prediction of protein conformation Biochemistry, 13(2):222–245 (1974).

Cigan et al.; Sequence and structural features associated with transitional initiator regions in yeast—A review; Gene, 59:1–18 (1987).

Cohen et al.; Alpha helical coils and bundles: how to design an alpha helical protein Proteins, 7:1–15 (1990).

Creighton, Thomas; Effects of urea and guanidine–HCl on the folding and unfolding of pancreatic trypsin inhibitor; J. Mol. Biol., 113:313–328 (1977).

Creighton, Thomas; Experimental studies of protein folding and unfolding Prog. Biophys. Molec. Biol., 33:231–297 (1978).

Creighton, Thomas; Interactions between cysteine residues as probes of protein conformation: The disulphide bond between Cys-14 and Cys-38 of the pancreatic trypsin inhibitor; Mol. Biol., 96:767-776 (1975).

Dacie et al.; Haemoglobin hammersmith (β42 (CD1) Phe —>Ser) Nature, 216:663-665 (1967).

Davis et al.; Structure of human tumor necrosis factor α derived from recombinant DNA Biochemistry, 26:1322-1326 (1987).

Bucci et al.; Pseudo cross-link of human hemoglobin with mono-(3,5-dibromosalicyl)fumarate J. Biol. Chem., 264(11):6191-6195 (1989).

Ackers et al.; The linkage between oxygenation and subunit dissociation in human hemoglobin PNAS 71(11):4312-4316 (1974).

Adams et al.; HB Mississippi [844(CD3)Ser-Cys]:A new variant with anomalous properties Hemoglobin, 11(5):435-452 (1987).

Barr et al.; Expression of active human immunodeficiency virus reverse transcriptase in S. serevisiae Biotechnology, 5:486489 (1987).

Beaucage et al.; Deoxynucleoside phosphoramidities—a new class of key intermediates for deoxypolynucleotide synthesis; Tet. Lett, 22:1859-1862 (1981).

Beggs et al.; Abnormal expression of chromosomal rabbit beta-globin gene in S. cerevisiae Nature, 293:834-841 (1980).

Behringer et al.; Synthesis of functional human hemoglobin in transgenic mice Science, 245:971-973 (1989).

Bellelli et al.; Cooperative ligand binding of crosslinked hemoglobins at very high temperatures J. Mol. Biol., 213:571-574 (1990).

Benesch and Benesch; The effect of organic phosphages from the human erythrocyte on the allosteric properties of hemoglobin; Biochem. Biophys. Res. Comm., 26(2):162-167 (1967).

Benesch et al.; Enhanced oxygen unloading by an interdimerically crosslinked hemoglobin in an isolated perfused rabbit heart; PNAS, 31:2941-2943 (1984).

Benesch and Kwong; Bis-pyridoxal polyphosphates: A new class of specific intramolecular crosslinking agents for hemoglobin; Biochem. Biophys. Res. Commun., 156(1):9-14 (1988).

Abu-Hadid et al, Selective Elimination of Idiotype-Binding Cells in Vivo by a Drug-Idiotype Conjugate Demonstrates the Functional Significance of these cells in Immune Regulation, Proc. Natl. Acad. Sci., USA, vol. 85, pp. 3990-3994, Jun. 1988.

Boger et al, Design of Proteolytically-Stable, Peptide Renin Inhibitors and Determination of their Fate in Vivo, Regulatory Peptides, Supplement, vol. 4, pp. 8-13, 1985.

Burgunder et al, Ethanol Decreases Plasma Sulphydryls in man: Effect of Disulfiram, European Journal of Clinical Investigation, vol. 18, pp. 420-424, 1988.

Fujita et al, Alteration of Biopharmaceutical Properties of Drugs by their conjugation with water-soluble Macromolecules: Uricasedextran Conjugate, Journal of Controlled Release, vol. 11, pp. 149-156, 1990.

Hwang et al, Identification of Residues Involved in the Binding of Hemoglobin a Chains to Haptoglobin, J. Biol. Chem., vol. 254, pp. 2265-2270, 1979.

Humphries et al, Investigation of the Biological Effects of Anti-Cell Adhesive Aynthetic Peptides that Inhibit Experimental Metastasis of B16-F10 Murine Melanoma Cells, J. Clin. Invest., vol. 81, pp. 782-790, 1988.

McCracken et al, An Enrichment Selection for Mutants Resulting from Oligonucleotide-Directed Mutagenesis of Double-Stranded DNA, Biotechniques, vol. 6, No. 4, pp. 332-334, 1988.

Luisi et al, Crystallographic Analysis of Mutent Human Haemoglobins made in Escherichia coli, Letters to Nature, vol. 320, No. 10 555-556, Apr. 1986.

Nagai et al, Distal Residues in the Oxygen Binding Site of Haemoglobin Studied by Protein Engineering, Letters to Nature, vol. 329, pp. 858-860, Oct. 1987.

Rettenmaier et al, Treatment of a Syngeneic Rat Tumor with Magnetically Responsive Albumin Microspheres Labeled with Doxorubicin or Protein A, Gynecologic Oncology, vol. 27, pp. 34-43, 1987.

Saiki et al, Inhibition of the Metastasis of Murine Malignant Melanoma by Synthetic Polymeric Peptides Containing Core Sequences of Cell-Adhesive Molecules, Cancer Research, vol. 49, pp. 3815-3822, Jul. 15, 1989.

Seymour et al, N-(2-Hydroxypropyl ) Methacrylamide Copolymers Targeted to the Hepatocyte Galactose-Receptor: Pharmacokinectics in $DBA_2$ Mice, Br. J. Cancer, vol. 63, pp. 859-866, 1991.

Thorpe et al, Improved Antitumor Effects of Immunotoxins Prepared with Deglycosylated Ricin A-Chain and Hindered Disulfide Linkages, Cancer Research, vol. 48, pp. 6396-6403, Nov. 15, 1988.

Wolfson et al, Insertion of an Elastase-Binding Loop into Interleukin-1α, Protein Engineering, vol. 4, No. 3, pp. 313-317, 1991.

Zoller et al. Oligonucleotide-Directed Mutagenesis of DNA Fragments Cloned into M13 Vectors, Methods in Enzymology, vol. 100, pp. 468-500, 1993.

Palca, Promising AIDS Drug Looking for a Sponsor, Science, vol. 253, pp. 262-263, Jul. 19, 1991.

Kida, Yoshitoshi, et al., "Vascular Responsiveness to Various Vasactive Substances After Exchange Transfusion With Pyridoxalated Hemoglobin Polyoxyethylene Conjugate (PHP) Solution In Anesthetized Rats", Chemical Abstracts, 115:17, abstract No. 175488k.

HEMOGLOBINS AS DRUG DELIVERY AGENTS

This is a division of copending application Ser. No. 08/240,711, filed Jul. 12, 1994, which is the national stage of PCT application PCT/US92/09713, filed Nov. 6, 1992, which is a continuation-in-part of both application Ser. No. 07/789,177, filed Nov. 8, 1991, now abandoned, and Ser. No. 07/789,179, filed Nov. 8, 1991, now U.S. Pat. No. 5,545,747.

CROSS-REFERENCE TO RELATED APPLICATIONS

Hoffman and Nagai, U.S. Ser. No. 07/194,338, filed May 10, 1988, now U.S. Pat. No. 5,028,588, presently owned by Somatogen, Inc. relates to the use of low oxygen affinity mutant hemoglobins as blood substitutes, and to the expression of alpha and beta globin in nonerythroid cells. Hoffman and Nagai, U.S. Ser. No. 07/443,950, filed Dec. 1, 1989, discloses certain additional dicysteine hemoglobin mutants; it is a continuation-in-part of Ser. No. 07/194,338. Hoffman, et al., Ser. No. 07/671,707, filed Apr. 1, 1991, which is the national stage of PCT/USO/02654, filed May 10, 1990, discusses expression of hemoglobins in yeast, polycistronic coexpression of alpha-and beta-globins and in vivo assembly of biologically active, tetrameric hemoglobin, and the production of di-alpha and di-beta globin pseudodimers and their use in the assembly of pseudotetrameric hemoglobins with increased intravascular retention. Hoffman, et al., Atty. Docket No. HOFFMAN5B-U. S. A., filed Nov. 8, 1991, entitled PRODUCTION AND USE OF HEMOGLOBINS AND ANALOGUES THEREOF, Ser. No. 07/789,179, is a continuation-in-part of Ser. No. 07/671,707, and discloses monocysteine mutants of hemoglobins and the production and use of octomeric and other multimeric hemoglobins built by use, e.g., of pseudodimers. The foregoing related applications are hereby incorporated by reference.

BACKGROUND OF THE INVENTION

1. Field of the Invention

The invention relates to the controlled release of drugs in the blood.

2. Description of the Background Art

Many pharmaceuticals have a relatively short half-life in the bloodstream due to renal clearance or rapid metabolisms. This is particularly true for polypeptide pharmaceuticals which are smaller than the renal filtration limit of about 50,000 to 70,000 daltons. In recent years, many pharmaceutical companies and other institutions have devoted considerable time and resources into extending the duration of a drug in the human body. The advantages of having a patient take a drug less often are numerous, such as, better compliance, more predictable concentrations in the body, and fewer side effects from the sudden rush of medication shortly after it is administered. All medications, especially those given prophylactically or for a long period of time, are more readily accepted by the patient if they need to be taken less often.

For medications which are given parenterally, every injection carries with it a chance for infection and imparts a certain amount of pain. Many patients are hospitalized simply because they need continuous or frequent injections of various pharmaceuticals. If the drug could be administered less often, some hospitalization costs may be avoided.

To overcome the problem of rapid removal of a drug from the body, one may give the patient very large doses so that the body receives an effective dosage for a longer period of time. However, the higher doses may result in more pronounced adverse effects.

Alternatively, one may include incorporation of the drug in a slowly dissolving or decomposing agent. The use of low-dose penicillins in ammonium sterate for the treatment of syphilis, and streptococcal infections, and for prophylaxis against rheumatic fever is one example; the use of Freund's adjuvant for, increasing the potency of vaccines is another. Polymers such as N-(2-hydroxypropyl)methacrylamide copolymers have also been proposed (Seymour et al, British Journal of Cancer, 63(6): 859–66 (1991)). Loose ion-ion bonding between drug and carrier has also been used for slow release of a pharmaceutical as described in U.S. Pat. No. 4,374,932. Some medications, such as contraceptives, are bound tightly to a carrier for very slow release over a period of months or years. The advantages in patient compliance over taking a pill everyday for the same period of time are readily appreciated. Another slow-release means is an insulin pump.

Clinicians have gone so far to ensure adequate long term dosage that they have even co-administered a different medication whose only purpose is to reduce the rate of excretion or metabolism of the primary drug. Administration of probenecid for the sole purpose of extending the half-life of high-dose penicillin and similar compounds in the body has been standard treatment for decades in treating gonorrhea and other disorders.

Just as medicinal chemists have been modifying a compound's structure to increase its potency, pharmacologists have been modifying compounds to increase their residency in the body. A very old example of this is the common drug acetylsalicylic acid (aspirin) which is a longer half-life derivative of salicylic acid. One approach has been to design the chemical so that it will more readily bind to certain serum proteins, thereby extending its half-life in the body. However, not all pharmaceuticals readily lend themselves to easy modification, and clinicians may desire a higher residency time than is achievable by simple drug modification alone.

Polypeptide pharmaceuticals pose special difficulties. In addition to the conventional problems of metabolism and renal clearance found with more conventional chemical drugs, body fluids contain endopeptidases such as serum dipeptidylpeptidase IV, as well as carboxy- and aminopeptidases. These can rapidly degrade many therapeutic peptides, many of which may have a free peptide half-life ($T_{1/2}$) in the range of minutes. Uptake by the liver and lipopilcity may also act to remove the polypeptide from its sites of action. (Boger et al., Regulatory Peptides, Supplement 4: 8 (1985)).

Derivatizing the polypeptide drug may reduce the rate of degradation. For example, N-acylation may block the action of aminopeptidases, and many carboxy terminal modifications have been proposed to limit carboxypeptidases. Additionally, use of numerous analogues of amino acids, some with unusual side chain moieties or non-peptide bonds, or of D-amino acids, has been proposed to inhibit proteolysis.

Biocompatable slow-release polymers may be used to release peptides over a period of time. Injectable poly-(D,L) lactic acid/glycolic acid copolymer microspheres have been used for slow release of a polypeptide over the course of a month. Polyethylene glycol and polysaccharide matrices have also been used for similar reasons (Hilvert, Trends in Biotechnology, 9(1): 11–17 (1991) and European Patent application 381,719). Surgically implanted polyanhydride disks or "hemispheres" have been experimentally used for slow release of large proteins over a one hundred day period of time. Other methods of drug delivery such as sublingual, oral adsorption and mucosal surface delivery have been explored using a number of potential agents but the slow-release effect has yet to be fully appreciated.

Biologically active polypeptides may be chemically bound to albumin via a linker which is non-cleavable, as discussed in European Patent Application 413,622 and Rettenmaier et al., *Gynecol, Oncol.*, 27(1): 34– 43 (1987). Biologically active material such as erythropoietin has been adsorbed onto or completed with albumin as well (U.S. Pat. No. 4,879,272 and 3,980,764) A number of other polypeptides and proteins have been proposed as drug delivery systems such as a part of fibronectin (Japanese patent 3,123,799 and 1,261,398, May 27, 1991 and Oct. 18, 1989), membrane proteins (German Patent 3,938,953), recombinant portions of elastase (Wolfson et al., *Protein Engineering*, 4(3): 313–317 (1991)), an assortment of lectins (European Patent Application 337,799), collagen (U.S. Pat. Nos. 4,291,013 and 4,849,141), various serum proteins and serum structures (U.S. Pat. Nos. 4,868,158, 4,842,856 column 2, line 3 and 4,918,008), and antibodies and their fragments, (Hadid, M. M. U.S. Pat. No. 4,474,893; *Proc Natl. Acad. Sci, USA*, 85(11): 3990–3994 (1988); European Patent Application 396,387 and PCT Application 91/09134) and other targeting proteins (European Patent Application 238,645).

Non-traditional peptides have been used as carriers for drugs as well. Tooth et al., attempted to increase membrane solubility by binding fatty compounds to a peptide using an amide, ester or other labile links to increase drug delivery. Similar systems have been used in U.S. Pat. Nos. 4,497,932 and 4,540,564. Attachment of a drug to functional groups located on the amino acid side chains of pseudopolyamino acids has been attempted.

Carbohydrates and other macromolecules have also been used as protein drug carriers. (Fujita et al., *Journal of Controlled Release*, 11 (1–3): 149–156 (1990)).

Drugs have been associated with various carriers in a number of ways such as: adsorption, entrapment, chemical linkage and within a liposome or vesicle. Some carriers are slowly adsorbed by the body and thereby release the drug as the carrier dissolves. Perhaps the most stable is by chemically bonding the drug to the delivery agent. However, too great of an attachment may mean that the drug is never released to the free, functional form. A number of linkages have been employed which include acid-labile and photo-labile bridges (European Patent Applications 185,762 and 191,772). Disulfide bonds are slowly cleaved in blood by low concentrations of reducing agents in serum such as glutathione, cysteine, homocysteine and gamma-glutanyl cysteine. Ester and peptide bonds are cleavable under acidic or alkaline, conditions, or by proteolytic degradation, all of which can occur in various parts of the body.

However, none of these agents are specifically confined to the bloodstream as many proteins tend to "leak" into the extravascular space. Furthermore, the release of the therapeutic agent from the delivery system is poorly controlled, and frequently, the nature of the attachment is random and not uniformly defined chemically. Moreover, the amount of a drug conjugated to the carrier is difficult to constrain, due to multiple, uncontrolled active sites on the carrier molecule, thus a mono-disperse formulation is not possible with the carriers mentioned above. All these factors may alter how the target drug is released.

In the field of imaging, similar problems are found. Many carriers for a tracer material have been used but have suffered from rapid clearance from the blood. Longer lasting carriers such as albumin (U.S. Pat. No. 4,042,677) have been tried but albumin lacks location specificity; it "leaks" from the bloodstream to give less than ideal images.

SUMMARY OP THE INVENTION

The present invention contemplates the use of hemoglobin as a carrier for drugs. Because hemoglobin is an endogenous, high molecular weight protein that can be modified in a site specific manner and expressed using recombinant technologies, unique and novel conjugates of drugs with hemoglobin-like proteins can be selectively designed that can be used to control the delivery of the drug by enhancing drug stability and increasing intravascular retention. Moreover, by appropriate selection of the conjugation site on the hemoglobin-like molecule and the linker molecule, one can achieve unique control over the behavior of the drug in vivo. In contrast to the various drug carriers used before, the present invention contemplates the use of hemoglobin as a carrier for any drug, especially drugs which are not themselves serum proteins, or which are serum proteins with a shorter intravascular retention time than that of normal human hemoglobin. Peptide drugs are particularly appropriate for delivery in this manner in view of their susceptibility to proteolysis in free form. This drug delivery system provides for stabilization and slow release of the drug in the bloodstream.

Since the intravascular half-life typically achieved with mutant hemoglobins is on the order of several hours, the present invention is most useful for the sustained delivery of drugs, especially peptide drugs, whose serum half life is less than one hour. However, the invention is not limited to the delivery of such drugs, particularly since the half-life of hemoglobin may be extended by mutation to retard haptoglobin binding.

Because hemoglobin is naturally found in the blood (as a result of erythrocyte aging) and not in the tissues, it is expected that the drug-hemoglobin conjugate will be retained in the bloodstream better than other protein carriers. Albumin and other proteins which move throughout the body are exposed to highly varied environments in each of the organs which may cause differing rates of drug release. By contrast, blood is relatively uniform other than in differences in oxygen tension between arterial and venous blood. Additionally, certain drugs are more toxic to certain tissues than others. By keeping the drug concentrated in the blood until it is slowly released, one may avoid much of the toxicity problems observed in the past. In addition, it becomes efficacious to administer lower potency drugs as high concentrations of free recombinant hemoglobin may be attainable in the blood.

The instant invention also contemplates protection of a biologically active molecule from degradation. Careful choice of the attachment site of the drug to hemoglobin by consideration of steric elements, electronic microenvironment, physical location on the hemoglobin, linker length, and attachment site on the target molecule can result in enhanced protection of the drug from endogenous removal mechanisms.

The present invention further contemplates substantially simultaneous delivery of a biologically active compound and oxygen. Certain chemotherapeutic agents are more effective in the presence of oxygen. Perfluorocarbons have been proposed to be administered after treating a patient with chemotherapy in hopes that the oxygen-deprived interior of a tumor will receive more oxygen and aid in the functioning of the chemotherapeutic agent. The current invention, not only may provide additional oxygen but may be used to release large amounts of oxygen and drug substantially simultaneously, and thus may enhance the efficacy of, e.g., chemotherapeutic agents.

It is yet another object of the invention to provide an imaging agent for measuring blood flow through various tissues.

Albumin, as a drug carrier, is inferior to hemoglobin in several respects. One not previously discussed in detail is that albumin contains 34 cysteines, which, in naturally folded albumin, participate in 17 disulfide bonds. If albumin is expressed in genetically engineered cells, so that one is not dependent on natural sources, the polypeptide will not necessarily fold as it does in human cells. The topology of disulfide bond formation may vary from molecule to molecule, resulting in a polydisperse composition. Some molecules will be unstable, resulting in early release of a conjugated drug.

If the cysteines of albumin are used as crosslinkable sites, then some will crosslink to the drug, and others to other albumin cysteines. Again, numerous variants will arise. Some will degrade rapidly; others will shield the drug so, well that it is not released in time to be useful. There will be no lot-to-lot consistency.

Each hemoglobin tetramer contains six cysteines: two in each beta globin subunit, one in each alpha globin subunit. Unless the tetramer is denature, only the beta 93 cysteine is reactive with reagents, and this cysteine may, as the drug designer desires, either be used as a crosslinking site, or neutralized by replacing it with a similar amino acid such as serine, alanine or threonine. It is much less likely that the many cysteines of albumin may be "neutralized" without affecting stability.

Because hemoglobin contains a small number of reactive thiols, and the number can be controlled by site-specific mutagenesis, it has a significant advantage over albumin.

DETAILED DESCRIPTION OF THE PREFERRED EMBODIMENTS OF THE INVENTION

The present invention relates to a system for delivering and/or stabilizing a ligand, such as a drug, by associating it, possibly through a linker, with a hemoglobin-like protein. These components—ligand, hemoglobin, and linker—will now be described in more detail.

Ligand

The chemicals being bound to hemoglobin may be very diverse in structure and function. Virtually any organic compound,including synthetic drugs, nucleic acids, polymers, other proteins, and especially a polypeptide or oligopeptide, may be associated with or bound to hemoglobin for stabilization, slow release, or localization to the vascular system or to, those tissues normally involved in hemoglobin degradation (liver, kidney, spleen). The use of the term "drug" in the description which follows is by way of example and not of limitation.

A number of bioactive peptides may be used as the peptide drug bound to hemoglobin. The following list is representative and not meant to be exhaustive of the potential drugs. The peptides shown are sometimes single examples taken from much larger sets of tested compounds to show the potential of the peptides as therapeutics. Prior to conjugation, however, analogs to these peptides may be constructed that will result in modified attachment sites, linker arms, spacers, or other elements necessary for suitable delivery with hemoglobin.

Either these peptides or other similar ones taken from the same classes may be readily synthesized by a peptide chemist having ordinary skill in the art. The invention is not limited however, to the delivery of peptide drugs.

A. Antithrombotics

1. RGDW (SEQ ID NO:1) or analogs thereof. This peptide blocks platelet aggregation mediated by platelet GPIIb/IIIa receptor-fibrinogen interaction. The $IC_{50}$ in mouse antithrombotic assay is 14 microM.

2. Ac-RGDY(Me)-$NH_2$ (SEQ ID NO:2) or analogs thereof. This compound blocks platelet aggregation as above with $IC_{50}$ of 10 microm. It is stabilized against plasma aminopeptidases by N-acetylation.

3. N-succinyl-YEPIPEEAA-Cha-$E_D$ (SEQ ID NO:3) or analogs thereof. The subscripted D represents the D-amino acid; the Cha is cyclohexylalanine. This compound is a synthetic inhibitor of human alpha-thrombin with $IC_{50}$ of 29 nM. It is also effective as an anticoagulant in mice. The compound is eliminated by the kidney; thus, attachment to and slow release from a larger molecule like Rb may dramatically extend serum half-life.

4. Ac-CRGD-penicillamine-$NH_2$ (SEQ ID NO:4) or analogs thereof. This compound has an $IC_{50}$ of 4 microM for blocking thrombus formation in dogs by intracoronary infusion. This compound may be linked to hemoglobin via the amino terminal cysteine.

B. Antiproliferatives or Antimetastics

1. Pr-HWAV$_4$AH (Me) L-OMe (SEQ ID NO:5) or analogs thereof. This compound has an $IC_{50}$ of 3.3 nM as an antagonist of bombesin-stimulated mitogenesis of Swiss 3T3 fibroblasts. Its half-life in rats is about 2.5 hours with subcutaneous administration. This drug was developed as a potential antagonist of gastrin releasing peptide, an autocrine growth factor in small cell lung cancer. A longer duration of action would be desirable.

2. (D-p-Cl-phe)-QWAVGH(beta-leu)-M-$NH_2$ (SEQ ID NO:6) or analogs thereof. This compound has an $IC_{50}$ of 0.8 nM for inhibition of gastrin releasing peptide binding, and 5.2 nM for inhibition of thymidine uptake by fibroblasts. Similar analogs have been shown to reduce imlanted tumor size in athymic mice.

3. [D-phe$^6$]-QWAVGHLM-$NH_2$ (SEQ ID NO:7) and [D-phe$^6$]-QWAVGHI-OMe (SEQ ID NO:8) or analogs thereof. This compound has an $IC_{50}$ of 243 and 29 nM and 2 nM and 0.167 nM for inhibition of bombesin release from guinea pig acini and inhibition of growth of Swiss 3T3 fibroblasts, respectively. The N-propyl amide analog has been injected into rats at 100 nmol/kg and blocked bombesin-stimulated pancreas amylase release for 60 min.

4. RGD polymers or analogs thereof. These compounds block lung tumor metastases in vivo; conditions which should increase peptide persistence in blood, such as multiple i.v. injections, increase efficacy, Saiki et al., *Cancer Res.*, 49: p.3815, (1989). Co- injection with the laminin sequence YIGSR may increase efficacy further. About 97% of the iodinated peptide is cleared from blood in 1 hour.

5. GRGDS or analogs thereof. This compound blocks metastasis of murine B16-F10 melanoma cells, Humphries, et al., J. Clin. Invest., 81: p. 782 (1988). Six micromoles (2.9 mg) of peptide (circulating half-life 8 min.) blocks metastases by 90t when counted 14 days later.

6. [p-$NH_2$]-FIGSR-amide or analogs thereof. This compound blocks melanoma metastases in mice. This peptide was designed as an antagonist of tumor cell laminin receptor binding to laminin in basement membranes.

C. Antihypertensives—Renin Inhibitors

1. Boc-HPFHL-CH(OH)-CH$_2$-VIH (SEQ ID NO:11) or analogs thereof. This compound has an IC$_{50}$ in vitro of 0.2 nM for inhibition of human plasma renin.

D. Human, Bovine or Ovine Growth Hormone Releasing Factor Analogs

1. HW$_D$AWF$_D$K-NH$_2$ (SEQ ID NO:12) or analogs thereof. This compound is a potent growth hormone releasing peptide in chicks, lambs, calves, pigs and rhesus monkeys. In the pig baseline growth hormone values are low and steady for extended periods. When administered alone without the drug delivery composition of the invention, intravenous, subcutaneous or intranasal injections produced sharp increases in plasma growth hormone levels (to about 45–75 ng/ml plasma) for varying periods of time, generally subsiding after about an hour. The doses ranged from 3–30 micrograms/kg (i.v.) to 25–100 micrograms/kg (s.c.) or 0.5 mg/kg (oral administration). Chronically increased levels may produce enhanced biological effects. This same peptide is hypothesized to have therapeutic use in humans as well.

2. $V^2$, $A^{15}$, $L^{27}$ bovine GRF (1-29)-NH$_2$ and $I^2$, $A^{15}$, L$^{27}$-bovine$_{GRF\ (1-29)}$-NH2 or analogs thereof. These peptides are highly potent, longer lasting (11–16 fold) bovine growth hormone releasing factor analogs resistant to plasma dipeptidylpeptidase IV. They are significantly more active in vivo in steers than the parent peptide, possibly due to longer plasma half-life and increased intrinsic potency.

E. Cholecystokinin Analogs e.g., as Anorexigenics

1. DY (SO$_3$) IGWMDF-NH$_2$ (SEQ ID NO:13) or DY (SO$_3$) NleGWNleDF-NH$_2$ (SEQ ID NO:14) or analogs thereof. This compound is a CCK-8 analog with anorexigenic effects by possibly binding to type-A CCK receptors and mediating satiety. The IC$_{50}$ for binding to pancreas, brainstem and pylorus type A receptors are 0.4–1.4 nM. Threshold anorexigenic doses are 0.05 nmol/kg in a rat model. A long lasting dose of these analogs in vivo may function effectively in a weight reduction program without major side effects.

2. Ac-Y$_D$(SO$_3$)MGWMDF-NH$_2$ (SEQ ID NO:15) or analogs thereof. The ED$_{50}$ in feeding assay is 1 microgram/kg intraperitoneal. High affinity agonists with 700-fold selectivity for the CCK-B receptors have been.developed using an N-methyl asp at the penultimate position. This could be combined with the sequence of the above antagonists for testing as a satiation-inducing drug.

F. Delta-Selective or Mu-Selective Eakephalin Analogs e.g., as Potential Analgesics 1. Cyclic oppugn$_D$GFPrn$_D$ [DPDPE] (SEQ ID NO:16) or analogs thereof. D-Pen is D-penicillamine. This is a cyclic enkephalin analog selective for delta-receptors over mu-receptors. This selectivity apparently avoids negative side effects associated with compounds such as morphine. N-terminal 2,6-dimethyltyrosine cyclic 4-mers and 5- mers, deltorphin I (Y$_D$AFDVVG-NH$_2$)(SEQ ID NO:17), and Phe$^3$ replacements of cyclic HC$_D$FPen$_D$ as potent delta agonists may also be used.

2. Phe$^3$ or leu$^3$-DPDPE or analogs thereof. This compound has delta vs. mu receptor selectivity and the above analogs appear to be completely inactive in binding the mu receptor. However the binding to delta receptor appears to be diminished (EC$_{50}$ is 100–200 nM in rat brain binding experiments). More potent analogs of deltorphin, including a substitution of asp$^4$ to ser$^4$, with an EC$_{50}$ of 0.36 nM, may also be used.

3. YA$_D$FEVVG (SEQ ID NO:18) (deltorphin B) or analogs thereof. This peptide has 3000–4000 fold selectivity for delta vs. mu receptors. The activity appears localized them the C-terminal tetrapeptide.

4. YR$_D$FK-NH$_2$ (SEQ. ID. NO: 19), a dermophin analog, or analogs thereof. This peptide is 11,000-fold selective for peripheral mu receptors over delta receptors, does not bind to peripheral kappa receptors, and does not appear to cross the blood/brain barrier apparently due to its net +2 to +3 charge at pH 7.4. It thus appears to function well as a peripheral antinociceptive, inducing analgesia with about the same potency as morphine although it is not as long lasting (Burgender et al., Eur. J. Clin Invest., 18; 420–4 (1988). Due to its peripheral action, it appears to lack some central side effects such as respiratory depression and dependence.

G. Vasoconstrictors

1. Epinephrine
2. Angiotensin II
3. Neuropeptide Y
4. Neurotensin
5. Arginine Vasopressin

H. Vasodilators

1. Atrial natriuretic factor
2. Angiotensin converting enzyme inhibitors
3. Renin inhibitors
4. Vasoactive intestinal peptide
5. Endothelin −1

I. Anti-AIDS Drugs

A very brief overview of current potential AIDS pharmaceuticals may be found in Science 253, 262–3, 1991.

1. HIV protease inhibitors. The HIV protease is involved in processing the precursor gag and gag-pol proteins into other proteins essential for virus assembly and replication. Inhibitors are thought to block integration of HIV into the cell's DNA and are in early clinical trials. Long term slow release of these inhibitors into the blood of AIDS patients using the delivery system of the invention may arrest the development of AIDS and allow attack on infected cells by other agents. For hemoglobin bound inhibitors injected as pharmaceuticals a very long half life in the range of weeks would be advantageous.

J. Non-(Human Drug) Ligands

In the field of agriculture, hemoglobin-stabilized compositions may be used therapeutically or prophylactically on both plants and animals. Growth enhancers, pesticides, herbicides, food and feed preservatives, topical cleaning agents, and veterinary pharmaceuticals, etc. may employ hemoglobin as a stabilizer and/or slow release agent.

Hemoglobin

An effective intravascular drug delivery agent must be readily conjugable to a wide variety of drugs, sufficiently soluble in blood to provide an effective dose of the drug in a reasonable volume of conjugate solution, and capable of delivering the drug over the extended period of time required to achieve the desired clinical effect. It also must be essentially non-immunogenic to the intended human or other animal subject. Preferably, the agent is also one which may be conjugated in a controlled manner, so that the formulator may conjugate the drug to predetermined sites with desired time release properties, and achieve a desired drug-to-carrier molar ratio. It is also desirable that the carrier be one which essentially does not leak out of the vascular system, so that the drug is not delivered to tissues prematurely. It is also helpful in some cases that the agent be one that reversibly binds oxygen, so that it may deliver oxygen to the drug's site of action.

In one embodiment, the intravascular drug delivery agent is a hemoglobin. Hemoglobins are oxygen binding proteins which take up oxygen at respiratory surfaces and deliver it to internal tissues. In another embodiment, the intravascular drug delivery agent is a globin, e.g., a myoglobin.

Hemoglobin is a protein which is highly soluble in aqueous media. Hemoglobin may be modified by site-specific mutagenesis to feature surface or crevice cysteine residues which may be reacted with thiol-bearing drugs, or with thiol-specific crosslinking reagents for conjugation to drugs. Since hemoglobin contains only two reactive cysteines per tetramer (at beta 93), the number of drug molecules conjugated, and the site(s) of conjugation, are readily controlled. Hemoglobins are well tolerated by the immune system; bovine hemoglobins have been used successfully in humans. While the data is imperfect, it is believed that there is substantially less leakage of hemoglobins from the vascular system than is the case with albumin. Hemoglobin is also a large enough protein so that, while an intact tetramer, it escapes revial filtration, however, it is too small to be scavenged by phagocytosis and similar mechanisms. (Hemoglobin may be modified to be more resistant to dissociation into diners and to binding by haptoglobin.) Finally, hemoglobin reversibly binds oxygen. These features, singly and in combination, are desirable in an intravascular drug delivery agent.

The structure of conventional hemoglobin is well known. We herewith incorporate by reference the entire text of Bunn and Forget, eds. *Hemoglobin: Molecular, Genetic and Clinical Aspects* (W. B. Saunders Co., Philadelphia, Pa.: 1986) and of Fermi and Perutz "Hemoglobin and Myoglobin," in Phillips and Richards, *Atlas of Molecular Structures in Biology* (Clarendon Press: 1981).

About 92% of the normal adult human hemolysate is Hgb A (designated alpha2 beta2, because it comprises two alpha and two beta chains). The alpha chain consists-of 141 amino acids. The iron atom of the heme (ferroprotoporphyrin IX) group is bound covalently to the imidazole of his 87 (the "proximal histidine"). The beta chain is 146 residues long (see FIG. 12) and heme is bound to it at his 92.

The primary structure of a polypeptide is defined by its amino acid sequence and by identification of any modification of the side chains of the individual amino acids. The local bending of the chain is its secondary structure. The tertiary structure of the hemoglobin molecule refers to the steric relationships of amino acid residues, while quaternary structure refers to the way in which the subunits (chains) are packed together. The tertiary and quaternary structure of the hemoglobin molecule have been discerned by X-ray diffraction analysis of hemoglobin crystals, which allows one to calculate the three-dimensional positions of the atoms of the molecule.

Hemoglobin is normally retained within erythrocytes, which have a life span of about 180 days. When erythrocytes age and die, they release hemoglobin into the bloodstream. There it dissociates into alpha-beta diners. The dimers are cleared either by renal filtration, or as a result of haptoglobin binding. The resulting complex has a serum half-life of about 10–30 minutes, as the complex is readily taken up by receptors on the Kupffer cells of the liver, where it is catabolized. Hemoglobin may also be removed from serum by other mechanisms, such as by liver parenchymal cell uptake of free hemoglobin.

The term "hemoglobin" as used in this application refers to a family of related molecules. Hemoglobin may be isolated from any animal (including human) source, produced artificially in recombinant organisms (including transgenic animals) or chemically synthesized.

For the purpose of the appended claims, a "hemoglobin" or "hemoglobin-like protein" is an oxygen binding protein with one or more heme prosthetic groups. Preferably, it comprises one or more heterotetramers composed of (a) two alpha globin-like and two beta globin-like polypeptides, (b) one di-alpha globin-like and two beta globin-like polypeptides, (c) two alpha globin-like and one di-beta globin-like polypeptides, (d) one di-alpha globin-like and one di-beta globin- like polypeptides, (e) one fused alpha/beta globin-like polypeptide and separate alpha and beta globin-like polypeptides, or (f) two fused alpha/beta globin-like polypeptides. A polypeptide of one tetramer may be crosslinked or genetically fused to a polypeptide of another tetramer. A hemoglobin is said to be multimeric if it comprises more than four globin subunits or domains. The term "multimeric" thereby includes octameric hemoglobin (2 linked tetramers), as well as higher multimers.

A human alpha globin-like domain or polypeptide is native human alpha globin or a mutant thereof differing from the native sequence by one or more substitutions, deletions or insertions, while remaining substantially homologous (as hereafter defined) with human alpha globin, and still capable of incorporating heme and associating with beta globin. A beta globin-like domain or polypeptide is analogously defined. Subunits of animal hemoglobins or mutants thereof which are sufficiently homologous with human alpha or beta globin are embraced by the term "human alpha or beta globin-like domain or polypeptide." For example, the subunits of bovine hemoglobin are within the scope of these terms. The alpha- and beta- globin-like polypeptides may be referred to collectively as "globins". For the sake of convenience the term "polypeptide" miay refer to a unitary chain or to a domain of a longer polypeptide chain.

A "genetically fused hemoglobin" is a hemoglobin-like protein comprising at least one "genetically fused globin-like polypeptide" (globin pseudooligomer), the latter comprising two or more globin-like domains which may be the same or different. A di-alpha globin-like polypeptide is one which consists essentially of two alpha-globin-like polypeptide sequences (domains) connected by peptide bonds between the normal C- terminus of the first alpha-globin-like polypeptide (domain) and the normal N-terminus of the second alpha-globin-like polypeptide (domain). These two sequences may be directly connected, or connected through a peptide linker of one or more amino acids; the term "peptide bonds" is intended to embrace both possibilities. Alpha globin chains crosslinked at the N- and C-terminals other than by peptide bonds (e.g., by DIDS) are not di-alpha globins. The di-alpha globin-like polypeptide preferably is capable of folding together with beta globin and incorporating heme to form functional hemoglobin- like protein. The di-beta globin-like polypeptide is analogously defined. A di-alpha or di-beta globin-like polypeptide with a mutation in only one of the component domains is called "asymmetric".

It is also possible to provide an "alpha/beta-globin-like pseudodimer" in which an alpha globin-like sequence is connected by peptide bonds to a beta globin-like sequence. This "alpha/beta globin-like polypeptide", and the di-alpha and di-beta globin-like polypeptides, may collectively be referred to as "pseudodimeric globin-like polypeptides" or as "diglobins". By extension, a hemoglobin-like protein comprising a di-alpha, a di- beta, or a alpha/beta globin-like polypeptide is a "pseudotetramer".

Even though the di-alpha hemoglobin does not dissociate into dimers, it is still cleared from the bloodstream, albeit more slowly than is the case for normal hemoglobin.

In determining whether a polypeptide is substantially homologous to alpha (or beta) globin, sequence similarity is an important but not exclusive criterion. Sequence similarity may be determined by conventional algorithms, which typically allow introduction of a small number of gaps in order to achieve the best fit. Preferably, the alpha-globin-like polypeptides or domains) of the present invention have at least about 75% sequence identity with wild-type human alpha globin. However, a polypeptide of lesser sequence identity may still be considered "substantially homologous" with alpha globin if it has a greater sequence identity than would be expected from chance and also has the characteristic higher structure of alpha globin and similar biological activity. By way of comparison, Artemia's heme-binding domains are considered homologous with myoglobin even though the primary sequence similarity is no more than 27%, as alignment of the heme- binding domains around their conserved residues and the residues conserved in other hemoglobins (i.e., involved in heme contacts or in determining the relationship of the helical segments to each other) suggested that the Artemia domains possessed the classical globin helices A to H with their corresponding turns, as well as various conserved globin family residues. Also, among the serine protease inhibitors, there are families of proteins recognized to be homologous in which there are pairs of members with as little as 30% sequence homology.

Well over a hundred mutants of human hemoglobin are known, affecting both the alpha and beta chains, and the effect of many of these mutations on oxygen-binding and other characteristics of hemoglobin are known. The human alpha and beta globins themselves differ at 84 positions. In addition, interspecies variations in globin sequence have been extensively studied. Dickerson, *Hemoglobin: Structure, Function, Evolution and Pathology*, ch. 3 (1983) reported that in 1982, the 60 known vertebrate alpha globins had identical residues at 23 of their 141 positions, while for the 66 vertebrate beta globins considered, 20 of the 146 amino acids are identical. The 60 vertebrate myoglobins, which also belong to the globin family, had 27 invariant amino acids out of 153 positions. If only mammals are considered, then the invariant amino acids are 50/141 for the alpha globins, 51/146 for the beta globins, and 71/153 for the myoglobins. Invariant positions cluster around the centers of activity of the molecule: the heme crevice and the intersubunit contacts. of the variable amino acids, some diverge from the consensus sequence for only a small fraction of the species considered.

The number of total differences between human alpha grlobin and selected other vertebrate alpha globins is as follows: rhesus monkey (4), cow (17), platypus (39), chicken (35), human zeta (embryonic) (61), carp (71), and shark (88). For invertebrate globins the divergences are sea lamprey (113), mollusc (124), Glycera (marine bloodworm) (124) and Chironomus (midge) (131). Turning to the beta globin family, the differences of human beta globin from other vertebrate beta globins are rhesus monkey (8), human delta globin (10), cow beta globin (25), cow gamma globin (33), human gamma globin (39), human epsilon (embryonic) globin (36), platypus (34), chicken (45), shark (96), sea lamprey (123), mollusc (127), Glycera (125) and Chironomus (128).

Many of these differences may be misleading—variable amino acids may exhibit only "conservative substitutions" of one amino acid for another, functionally equivalent one. A "conservative substitution" is a substitution which does not abolish the ability of a giobin-like polypeptide (or domain) to incorporate heme and to associate with alpha and beta globin subunits to form a tetrameric (or pseudotetrameric) hemoglobin- like protein which, in keeping with the definition thereof, will reversibly bind oxygen. The following resources may be used to identify conservative substitutions (and deletions or insertions):

(a) data on functional hemoglobin mutants (over a hundred such mutants exist);

(b) data on sequence variations among vertebrate, especially mammalian, alpha globins and beta globins;

(c) data on sequence variations among vertebrate, especially mammalian, myoglobins;

(d) data on sequence variations between vertebrate and invertebrate globins, or among the invertebrate globins;

(e) data on the three-dimensional structures of human hemoglobin and other oxygen-binding proteins, and molecular modelling software for predicting the effect of sequence changes on such structures; and (f) data on the frequencies of amino acid changes between members of families of homologous proteins (not limited to the globin family). See, e.g., Table 1–2 of Schulz and Schirmer, *Principles of Protein Structure* (Springer-Verlag: 1979) and FIG. 3–9 of Creighton, *Proteins: Structure and molecular Properties* (W. H. Freeman: 1983).

While the data from (a)–(d) is most useful in determining tolerable mutations at the site of variation in the cognate proteins, it may also be helpful in identifying tolerable mutations at analogous sites elsewhere in the molecule. Based on the data in category (f), the following exchange groups may be identified, within which substitutions of amino acids are frequently conservative:

I small aliphatic, nonpolar or slightly polar residues—Ala, Ser, Thr (Pro, Gly)

II negatively charged residues and their amides—Asn Asp Glu Gln

III positively charged residues—His Arg Lys

IV large aliphatic nonpolar residues—Met Leu Ile Val (Cys)

V large aromatic residues—Phe Tyr Trp

Three residues are parenthesized because of their special roles in protein architecture. Gly is the only residue without a side chain and therefore imparts flexibility to the chain. Pro has an unusual geometry which tightly constrains the chain, Cys can participate in disulfide bonds which hold proteins into a particular folding. Note that Schulz and Schimer would merge I and II above. Note also that Tyr, because of its hydrogen bonding potential, has some kinship with Ser, Thr, etc.

In general, functionality is less likely to be affected by mutations at surface residues, at least those not involved in either the heme crevice or the subunit contacts. In addition, "loops" connecting alpha helices, as well as free amino or carboxy termini, are more tolerant of deletions and insertions.

When administering a drug bound to a hemoglobin to an animal, it is preferable to use a hemoglobin which is not significantly antigenic to the recipient animal. When the hemoglobin is not being used in or on an animal body, the type of hemoglobin is less critical provided that it adequately stabilizes the chemical. While it is preferred that the hemoglobin remains capable of binding oxygen, that is not a strict requirement.

Hemoglobin is readily available from a number of sources. Slaughter houses produce very large quantities of hemoglobin in the form of blood which is currently usually sold as an inexpensive fertilizer. If particular species or breed of animal produces a hemoglobin especially suitable for a particular use, those creatures may be specifically bred for this purpose, in order to supply the needed blood. Human blood banks must discard human blood after a certain expiration date. This also produces large quantities of hemoglobin. Techniques for the isolation of hemoglobin from blood are known per se. Any of the published or standard techniques may be used.

In addition to extraction from animal sources, the genes encoding subunits of a desired hemoglobin may be cloned, placed in a suitable expression vector and inserted into an organism, such as a microorganism, animal or plant, or into cultured animal or plant cells or tissues. These organisms may be produced using standard recombinant DNA techniques. Human alpha and beta globin genes have been cloned and sequenced by Liebhaber et al., *Proc. Natl. Acad. Sci. USA*, 77; 7054–7058 (1980) and Marotta et al., *Journal of Biological Chemistry*, 252; 5040–5053 (1977) respectively. Techniques for expression of both wild-type and mutant alpha and beta globins, and their assembly into a functional hemoglobin, are set forth in the related applications cited above.

Hemoglobin $A_o$ is a heterotetramer composed of two alpha globin subunits ($\alpha_1$, $\alpha_2$) and two beta globin subunits ($\beta_1$, $\beta_2$). There is no sequence difference between $\alpha_1$ and $\alpha_2$, or $\beta_1$ and $\beta_2$. In the unoxygenated ("deoxy", or "T" for "tense") state, the subunits form a tetrahedron. The $\alpha_1 \beta_1$ and $\alpha_2 \beta_2$ interfaces remain relatively fixed during oxygen binding, while there is considerable flux at the $\alpha_1 \beta_2$ and $\alpha_2 \beta_1$ interfaces. In the oxygenated ("oxy" or "R" or relaxed) state, the intersubunit distances are increased. The subunits are noncovalently associated by Van der Waals forces, hydrogen bonds and, for deoxy Hgb, salt bridges. Hemoglobin is known to dissociate into $\alpha_1 \beta_1$ and $\alpha_2 \beta_2$ dimers, which are eliminated from the bloodstream by renal filtration. In travascular retention of hemoglobin has been improved by, e.g., chemical crosslinking of subunits of a single tetramer, or between tetramers.

As taught in the related applications, it is possible to produce a pseudotertrameric hemoglobin in which two non-covalently assoicated subunits are replaced by a single pseudodimeric polypeptide with two oxygen binding domains, joined either directly or by a linker of one or amino acids. This pseudodimeric polypeptide may be expressed from a suitable fused gene. Thus, two alpha globin genes may be fused into a "di-alpha golbin" gene, or two beta globin genes into a "di-beta globin" gene, or alpha and beta globin genes into an "alpha beta" globin pseudodimer gene.

The advantage of fusing two or more globin chains together is that one can selectively mutate one but not both of the chains, as taught in HOFFMAN SB. This permits one to provide only one attachment site for the drug of interest so that equimolar amounts of drug and hemoglobin are found in the final product.

Another alternative is to have numerous attachment sites on the hemoglobin molecule. This would permit stabilization of higher amounts of the chemical being bound, and probably different release rates of the bound drug.

Hemoglobin has been modified using many techniques in the past. Any of these techniques may be used to prepare the hemoglobin component of the drug-hemoglobin conjugate of the invention. Examples of such modifications are found in U.S. Pat. Nos. 4,412,989, 4,301,144, 4,670,417, 4,321,259, 4,473,563, 4,710,488, 4,650,786, 4,336,248, 4,598,064, 4,600,531 and 4,377,512 among others. Individual globin chains have been reasserted with modified forms to synthesize a semi-synthetic hemoglobin as well (Luisi et al., *Nature*, 320; 555–556 (1986) and Nagai et al., *Nature*, 329; 858–860 (1987)). Other modifications such as polymerization of globin chains, glycosylation, pegylation, encapsulation in a liposome or cell membranes are also contemplated.

The hemoglobin produced by expression of recombinant DNA also lends itself to easy modification. By applying the standard techniques of site specific mutagenesis to the globin gene(s), (McCracken et al., *Biotechnicues*, 6; 332–339 (1988) and Zoller et al., *Methods in Enzymology*, 100; 468–500 (1983) are recent examples) one can add, subtract or change any amino acid or combination of amino acids in the resulting globin chain. The modified portions may constitute an attachment site for the drug of interest. This may alter the number and locations where the drug is associated with or binds to the hemoglobin molecule. If the drug of interest is itself a polypeptide, one may add it onto the globin chain to yield a drug-hemoglobin conjugate.

Chemically crosslinked hemoglobins, or mutant hemoglobins which genetically fuse the alpha subunits (di-alpha Hgb) or the beta subunits (di-beta Hgb), may increase intravascular retention by inhibiting haptoglobin binding. While a di-alpha hemoglobin apparently is still bound by haptoglobin, most likely through breathing of the hemoglobin tetramer, the rate is much slower than for $A_o$, the di-alpha Hgb remaining in the bloodstream for several hours. For drug delivery when haptoglobin binding to hemoglobin is not desired, this technique may be used.

Any of the hemoglobins or fragments thereof may be modified to alter the biological activity of the hemoglobin itself. U.S. Pat. No. 5,028,588 teaches use of low oxygen affinity mutants as blood substitutes. Such a modified molecule may then be conjugated to a drug to form the drug-hemoglobin conjugate of the invention.

Linkage of the Ligand to the Hemoglobin

The ligand may be a) covalently bound, directly or indirectly; b) noncovalently bound, directly or indirectly, erg., by hydrogen bonds, van der Waals forces, or hydrophobic interactions; or c) physically trapped in the three dimensional network of the hemoglobin or a trapping means associated with the hemoglobin. The coupling may be direct, or indirect by way of a linker moiety or intermediate binding molecule associated with both the drug and the hemoglobin.

Covalent Attachment. In one embodiment, there is a covalent attachment of the ligand to the hemoglobin. This attachment may arise through direct reaction of a functionality on the ligand with a functionality on the hemoglobin, or by reaction of the ligand and the hemoglobin, simultaneously or in any order, with a homofunctional or heterofunctional bridging agent. If the ligand or hemoglobin lack the desired functionality, it may be provided by derivitization of the ligand or hemoglobin.

Preferred hemoglobin attachment sites include a cysteine which can form a disulfide bond and amino acids with a free carboxylic acid or amine moiety, such as aspartic acid and lysine, which can react with the drug to form an ester, peptide or other bond.

Disulfide Bonds. The use of a disulfide bond to form the attachment is especially preferred. A disulfide bond may be formed between a thiol side group of a cysteine residue of the hemoglobin, and a thiol group on the ligand. The advantage of the disulfide bond is that it will be slowly reduced by reducing agents endogenous to serum, thereby providing for the slow release of a liganded drug into the bloodstream. Reagents and conditions for formation of disulfide bonds are well known in the art. Cysteines may be introduced into hemoglobin, by substitution or insertion, for this purpose.

Modulation of Disulfide Bond Stability. The delivery of the drug or rate of release of the chemical would be affected by both the steric and electronic factors influenced by the location of the linkage on the hemoglobin chain(s). In order to have the chemical more slowly released, one could flank the thiol of the drug with a bulky chemical moiety to hinder biochemical reduction of the disulfide bond. For example, in the case of a peptide drug, the drug could feature a crosslinkable cysteine adjacent to a bulky residue such as tryptophan or beta-naphthylalanine. The half-life of disulfide linkages between a monoclonal antibody and ricin A chain has been measured in mice as 6.7 hours (Thorpe et al., *Cancer Research*, 48: 6396 (1988)). However, when using a sterically hindered disulfide with an alpha-methyl substituent next to one sulfur, a 6.3-fold longer half-life was observed. The same substituent may be used for the present invention as well.

Alternatively, the hemoglobin cysteine could be partially concealed in the middle of a globin chain, next to a branched portion, in a cleft between two chains, or surrounded by negatively charged residues such as aspartic acid or glutamic acid, to repel negatively charged reducing compounds. All of these techniques may be used to kinetically increase the disulfide bond's half-life in a reducing environment. The particular chemical being attached to a hemoglobin chain and the desired half-life of the chemical would determine which combination to use. This could be easily determined using routine experimentation.

Besides the drug of choice, one may crosslink a reducing or oxidizing agent to the hemoglobin molecule. If a reducing agent is crosslinked, the initial rate of drug release will be slow, but, once the reducing agent is released, it will accelerate the rate of drug release by attacking the disulfide bond. A released oxidizing agent will have the opposite effect.

The profile of drug release may also be modified by attaching drugs to different sites, of varying accessibility, on the same or different hemoglobin molecules.

Attachment Sites on the Hemoglobin Molecule. In one embodiment, the attachment site is on the outside portion of the hemoglobin molecule so that the ligand may attach to it more easily. The attached ligand would have an enhanced half-life and might retain activity when still attached to the hemoglobin. Alternatively, if one wished to protect the chemical from degradation, and/or achieve an even longer half-life of the drug, a less accessible site on the hemoglobin molecule may be used.

Surface Cysteines. A variety of sites are available for introduction of surface cysteines into a hemoglobin-like protein.

The criteria governing site selection are: (1) the mutation does not affect functionality; (2) the side chain is accessible to water in oxy or deoxy structure; (3) the site should lie on the surface of the folded protein; (4) the sulfhydryl of the side chain should extend away from the surface rather than toward the interior of the molecule; (5) the site should be in a portion of the molecule that is not directly invovled in the R-→T transition; (6) the change should be in a portion of the molecule that does not have a tightly fixed position (such regions generally give indistinct X-ray diffraction patterns); (7) the mutations will not destroy the local secondary structure, i.e., avoid pro-→cys mutations, which might result in a refolding problem;. and (8) if possible, a conservative change should be made such as ser-→cys or ala→cys. A mutation does not necessarily have to meet all of the above requirements to be useful. For example, one might envision a site that is involved in the R-→T transition (cf. 5 above) but confers a beneficial change in $P_{50}$ (cf. 1 above) because of that involvement. The most important considerations are that the mutation does not abolish $O_2$ binding, before or after crosslink formations, and that the cysteine is accessible for participation in the desired crosslinking reaction.

Candidate sites on the alpha surface include:

his72, asn 78, asn68, ala71, thr67, lys7, lys11, thr8, ala12, thr118, lys16, ala45, glu116, gly15, his112, thr24, glu23, lys60, lys56, his50, gly50, glu53, ser49, asp47, gln54, his45, lys90, ala82, lys61, ala19, his20, asp85, ser81, asp75, asp74, Lys139, asp64, and gly18 (total 40 amino acids).

Candidate sites on the beta surfaces includes:

asp79, his2, leu3, thr4r glu6, ser9, thr12, ala13, gly16, lys17, val18, asn19, val20, asp21, glu22, lys65, ser72, ala76, his77, asp79, asn80, gly83, ala86thr87, glu90, lys95, lys59, glu43, ser44, asp47, ser49, thr50, ala53, asp52, lys61, glu121, lys120, thr123, lys66, asp73, ala62, his116, his117 (total 45 amino acids).

There are a number of naturally occurring mutants which already show mutations at these sites. These are listed below:

| Residues | Region | Mutation |
|---|---|---|
| 19 | AB1 | ALA->GLU |
| | | ALA->ASP |
| 54 | E3 | GLN->ARG |
| | | GLN->GLU |
| 71 | E20 | ALA->GLU |
| 75 | EF4 | ASP->GLY |
| | | ASP->HIS |
| | | ASP->TYR |
| | | ASP->ASN |
| 81 | F2 | SER->CYS |
| 47 | CE5 | ASP->GLY |
| | | ASP->HIS |
| | | ASP->ASN |

Surface or near-surface cysteine mutations in general are not expected to have major effects on the functionality of the hemoglobin pseudotetramer. Cysteine mutations would not be expected to significantly destabilize alpha helices, and surface residues are not directly involved in the oxygen binding properties of hemoglobin. Most surface residues undergo considerable motion and are not tightly constrained. It should also be noted that because of protein breathing motions, the cysteine side chain would not necessarily have to point directly into solution to be accessible for disulfide bond formation.

Mutations to Protect the Disulfide Bond. In serum, disulfide bonds are reduced by endogenous thiols, such as glutathione. The mechanism of these reactions involves the thiolate anion as the actual reducing species (Creighton, T. E. (1978) *Prog. Biophys. Molec. Biol.*, 33:259–260 231–297; Creighton, T. E. (1975) *J. Mol. Biol.;* 96:767; Creighton, T. E. (1977) *J. Mol. Biol.*, 113:313). Thus the rate of reduction will be a function of the molecular electrostatic environment in the vicinity of the disulfide bond. A slower rate of reduction would be predicted if the disulfide was located in an electrostatically negative environment,, due to the repulsion of the thiolate anion. In the case of glutathione, even the unreactive transient protonated species has a net negative charge and would be repulsed, thus further reducing the rate of disulfide reduction.

A surface or near-surface amino acid residue of di- alpha or di-beta hemoglobin that is located in close proximity to a negatively charged surface residue might therefore be a good choice for location of a single cysteine mutation. Although formation of the initial disulfide bond between two such cysteines might also be slower because of repulsion between the negative charges on the two hemoglobin molecules in the vicinity of the cysteines, the reaction could be facilitated by use of high salt or high pH during the in vitro bond formation reaction. If carried out under deoxy conditions in a redox buffer, the reaction might also be facilitated by temperature elevation.

| Preferred sites for cys mutations proximal to negative charged residues | |
|---|---|
| alpha ser49 | near asp47; naturally occurring ser49 to arg has normal $O_2$ affinity |
| alpha his20 | near glu23; naturally occurring his20 to tyr, gln, arg have no known undesirable properties |
| alpha lys16 | near glu116; naturally occurring lys to glu has normal $O_2$ affinity |
| alpha his50 | near glu30; naturally occurring his50 to asp has no known undesirable properties |
| beta thr50 | near asp52; naturally occurring thr50 to lys has no known undesirable properties |
| beta lys65 | near asp21 |
| beta asn19 | near asp21 |

Crevice Cysteine Mutants. Crevice-cysteine hemoglobin mutants are also of interest and are prepared by site specific mutagenesis. The mutant crevice cysteine is then disulfide bonded to the drug. The walls of the crevice will sterically hinder attack by serum reducing agents on the drug-hemoglobin disulfide bond.

Such a crevice exists in the deoxy structure of hemoglobin. In this structure, replacement of residues at the bottom or sides of the crevice (such as alpha leu 34, alpha 40 lys, beta 132 lys, or alpha 37 pro, in each case mutated to cys) would yield attachment sites giving very slow release from the deoxy structure. For example, the surface of the deoxy structure suggests that alpha 34 leu acys mutation might form a disulfide deeply embedded in a cleft in deoxy Ao. The mutation to arginine does not affect stability or oxygen affinity. (Alpha lys 139 is implicated in haptoglobin binding Lumeng, (J. Biol. Chem. 254, 7265, 1969) and is also slightly in a cleft.)

The crevice in the oxy structure of hemoglobin is much less deep, suggesting that the disulfide bond anchoring the peptide or drug to oxyhemoglobin will be more accessible to reductants. Thus, the rate of release of a drug bound to a deoxyhb crevice cysteine will be controlled by the percent of time the structure is in the deoxy conformation, which is a function of P50 of the hemoglobin.

An additional crevice is the hole in the center of deoxy hemoglobin. Mutation of individual residues in this hole to cysteine would yield extremely slow rates of release by reduction of the peptide-or drug-disulfide bond to the mutant. Such attachment sites would have an additional advantage that the peptide attached here would likely be protected from proteolysis when attached. Sites of such mutations include alpha lys 99, thr 134 and beta arg 104, his 143, lys 82 and asn 139. These mutations could be combined for attachment of more than one peptide to the hemoglobin.

Due to the high positive charge density in this hole, attachment could be stabilized by addition of one or more negatively charged moieties to the peptide. Linear peptides with an N- or C-terminal Cys and without bulky residues in the first three or four amino acids are those most likely to fit into this hole.

Low oxygen Affinity Mutations. The deoxy confomation may be stabilized by introduction of low oxygen affinity (high $P_{50}$) mutations to a cysteine mutant. The lower the affinity of the resulting hemoglobin, the slower the release rate of drug. This mechanism should allow release of drug more selectively at tissues with a high partial pressure of oxygen, such as in the vasculature of the lungs.

Candidate mutations for diminishing the affinity of hemoglobin include the Presbyterian mutation (measured P50 of pure hemoglobin of 35 mm Hg), beta 67 val to ile (P50 of 24.7 mm Hg), hemoglobin Kansas (P50 of ca. 20 mm Hg[a]), hemoglobin J-Cairo (P50 of 15 mm Hg[a]), hemoglobin Titusville (P50=16 mm Hg[a]), Hemoglobin Beth Israel (P50 of whole blood=88 mm Hg[a]), for example. Combination of these mutations might be expected to yield mutants with lower oxygen affinities. ([a].ref. is Bunn and Forget, Hemoglobin: Molecular, Genetic and Clinical Aspects, 1986, Philadelphia: W. B. Saunders, p. 615).

An additional method to form a hemoglobin with a very low oxygen affinity includes insertion of a disulfide bond across subunit interfaces which move in the R to T state transition of hemoglobin. Disulfides which form in the T state across the alpha 1-beta 2 interface would stabilize the T (deoxy) state and thus diminish the P50 of the protein. One example of such a disulfide bond, obtained by inspection of the deoxy structure, would result from the mutations alpha 96 val→cys and beta 101 glu→cys.

Other examples, obtained to satisfy several geometric criteria for disulfide formation, (i.e., Calpha-Calpha distances of less than 7.4 A, Cbeta-Cbeta distances between 3.3 and 4.6 A, and the angles between Calpha2, Cbeta2 and Cbeta1 and the angles between Calpha1, Cbeta1 and Cbeta2 are between 53 and 180 degress, are listed below (ref.: Balaji et al., Biochem. Biophys. Res. Comm. 160, 109–114, 1989). These include beta 37 trp to cys and alpha 92 arg to cys; beta arg 40 to cys and alpha arg 92 to cys; and beta his 97 to cys and alpha thr 41 to cys. To obtain maximum stabilization of the T state, these mutations should be introduced into both beta and alpha domains. If these disulfide bonds form, the structure would be locked in the deoxy conformation, and the resultant P50 would probably be quite high (over 100 mm Hg).

Mutations Which Inhibit Haptoglobin Binding. A cysteine to form a disulfide bond located on the surface of the molecule located in a position to block haptoglobin binding is also possible. Molecular graphics suggest residues around alpha lys 139 such as lys 90 or ala 82 are candidates for mutation to cysteine so that a recombinant hemoglobin bound to the desired chemical may prevent haptoglobin binding. The preferred residues to be mutated to cysteines include alpha 1, 6, 74, 85, 89, 93, 118, 120–127, 138–141, and beta 2, 11–25, 31–40, and 131–146. The first and latter two regions are on or near the surface of the beta chain. These hemoglobins may be checked for inhibition of the initial rate of haptoglobin binding, observed by fluorescence quenching of haptoglobin (Hwang and Greer, J. Biol. Chem. 254, 2265, (1979)) by attachment of peptides for drug delivery.

Derivatization of the Ligand for Crosslinking to Hemoglobin. If the ligand being bound does not naturally have a free sulfhydryl or similar attachment moiety, the ligand may be modified to add such a moiety. In the example of a polypeptide drug being stabilized, the addition of an amino terminal or a carboxy terminal or internal cysteine is easily performed by solid phase peptide (Merrifield) synthesis. Moreover, if the target ligand is not long enough or must be otherwise separated from the carrier hemoglobin, then suitable linking amino acids can be added to the attachment site, for example, a polyproline linker may be designed after the disulfide bond between the hemoglobin and the polypeptide. The addition of amino acid linker tails might enhance the stability of the polypeptide drug by reducing susceptibility to endogenous protease degradation. Suitable "secondary linkers" such as D-amino acid chains or polyproline chains can be envisioned.

The preferred method of obtaining a disulfide bond is a function of the drug:

LINEAR PEPTIDE DRUG WITH ONE Cys: form disulfide bond between drug. Cys and henoglobin Cys.

LINEAR PEPTIDE DRUG WITH NO CYS: A cysteine is introduced into the drug, e.g., by one of the following methods: (a) Cys is added (with or without one or more glycine spacers) to N- or C-terminus of drug; (b) a non-critical residue of the drug peptide sequence is replaced with cys; (c) a cys is added as a branch off a lys-$\epsilon$-$NH_2$ group in the peptide. The introduced Cys is then disulfide bonded to the hemoglobin Cys.

CYCLIC PEPTIDE WITH NATURALLY OCCURRING DISULFIDE: One may proceed by (a) addition of cys (Npys) [to protect disulfide and thus prevent thiol-disulfide interchange which would open ring] at N- or C-terminus or replacement of non-critical residues in ring with Cys, or (b) construction of non-reducible rings, and placement of cys at N- or C-terminus or replacement of non-critical amino acids in ring. In this case, the reducible disulfide (—S—S—) bond is replaced by, e.g., (1) a thioether (—S—), (2) a lactam ((K)-NHCO-(D)) or (3) methylene (—$CCH_2$)$_m$) structure.

NON-PEPTIDE DRUGS: If the drug contains a free thiol, this may be reacted with the thiol of the hemoglobin cysteine. If not, the drug must be synthetically modified to contain a free thiol. It may be possible to replace a hydroxyl group with a thiol group, or it may be desirable to add a thiol-bearing moiety to the drug.

It should be understood that it is desirable that whatever modifications are made to the drug to permit crosslinking are selected with a view to conserving the biological activity of the unmodified drug. It is not necessary that the drug be active while conjugated to the hemoglobin, provided that it is active once released.

Non-Disulfide Crosslinks. While disulfide linkages are preferred because in vivo reducing agents act to liberate the peptide from the carrier or exogenous reducing agents can be co-administered to modulate half-life, any labile linkage or reversible association may be used. Peptides and other organic compounds may be attached to hemoglobin by alkylation of the cysteine with haloacetyl-peptides or haloacetyl-compounds obtained by direct synthesis. Bifunctional crosslinkers may also be used to bind a chemical to a hemoglobin chain. Yet another example is ester linkages to be cleaved in acidic or alkaline environments. Certain protease cleavage sites for serum proteases could be used as the linker to permit release of the desired chemical. The surrounding microenvironment may be modified by site specific mutagenesis or chemical modification to achieve the desired release rate.

Fusion Proteins. When the ligand is a polypeptide or oligopeptide, it is possible to provide the ligand-hemoglobin conjugate in the form of a fusion protein, wherein the ligand is incorporated into the alpha and/or beta globin chains as a new domain thereof. The ligand may be inserted at an interhelix loop, or it may replace a nonessential structure such as the globin D-helix. The ligand may be attached to the remainder of the chimeric globin chain by a peptide linker of one or more amino acids, e.g., glycines.

Non-Covalent Attachment. In another embodiment, the ligand and hemoglobin are noncovalently attached. Attachment may be indirect such as attaching the ligand to a molecule which in turn adsorbs itself onto hemoglobin. For example, one may bind a drug (covalently or noncovalently) to an anti-hemoglobin antibody which in turn noncovalently binds to the hemoglobin molecule. Avidin/biotin binding may also be used with one of the two bound to hemoglobin and the other bound to the ligand. Also one may bind the drug to haptoglobin which naturally binds to hemoglobin. A fragment of haptoglobin containing the binding site is also acceptable as an attachment means. These associations preferably occur before being added to the situation of the chemical's use, however the association may also be formed in situ.

Noncovalent associations may be formed directly, e.g., through hydrogen bonding and hydrophobic forces associating the hemoglobin with the ligand. Using site specific mutagenesis, one could, for example, have a number of hydrophobic amino acids in close proximity to each other to encourage attachment of a hydrophobic portion of the desired chemical. Close proximity need not imply that the amino acids are adjacent in the chain; rather, the whole molecule may place two separated amino acids in close proximity due to the secondary, tertiary or quarternary structure.

Miscellaneous. Ideally, the half-life of the pharmaceutical in the animal would be at least several days for drugs one wishes to act over a period of time, such as Peptide T. However, when the delivery of drugs for shorter periods is desired, such as for tissue plasminogen activator, a different choice of hemoglobin delivery vehicle would be preferable. It may be desirable to use two different types of linkages or different hemoglobin delivery agents, each with a different half-life, to extend the effective concentration of the drug. This may involve two administrations, one administration with two different hemoglobin stabilizers or one hemoglobin delivery agent having plural non-identical sites for attachment of the desired chemical. The stabilization composition may contain one or more additional chemicals as well.

Compositions and Use Thereof

The present invention also provides pharmaceutical compositions and formulations for prophylaxis and treatment of many diseases using the drug-hemoglobin conjugate. The compositions of the invention can be incorporated in conventional solid or liquid pharmaceutical formulations (e.g. tablets, capsules, caplets, injectable or orally administrable solutions) for use in treating mammals in need thereof. The pharmaceutical formulations of the invention comprise an effective amount of the drug-hemoglobin conjugate of the present invention as the active ingredients alone or in combination with other- active or inert agents. For example, a parenteral therapeutic composition may comprise a sterile isotonic saline solution containing between 0.1 percent and 90 percent of drug-hemoglobin conjugate. The quantity of pharmaceutical provided to the individual is sufficient to provide a blood concentration of between 0.001 micromolar and 1 millimolar of drug-hemoglobin conjugate. It will be appreciated that the unit content of active ingredients contained in an individual dose of each dosage form need not in itself constitute an effective amount since the necessary effective amount can be reached by administration of a plurality of capsules, tablets, injections, etc. or combinations thereof.

Each formulation according to the present invention may additionally comprise inert constituents including pharmaceutically-acceptable carriers, diluents, fillers, salts, and other materials well-known in the art, the selection of which depends upon the dosage form utilized, the condition being treated, the particular purpose to be achieved according to the determination of the ordinarily skilled artisan in the field and the properties of such additives.

The pharmaceutical compositions of the invention may be administered to an individual by any conventional means such as orally, by aerosol, by transdermal adsorption, by adsorption through a mucus membrane or by injection. Parenteral administration is preferred, particularly intravenously or intraarterial.

Another preferred embodiment of the invention is to use hemoglobin as a carrier for a diagnostic imaging agent. The diagnostic agent may be radioactive for radiodiagnostic imaging. A radioactive atom containing molecule may be incorporated into hemoglobin ($^{99m}$Te, $^{55}$Fe, etc.) during synthesis or separately bound to hemoglobin later. Technetium-99m is an example of a preferred radioactive agent which has become popular in recent years because of its short half-life and easily detected signal. For performing magnetic resonance imaging, any paramagnetic element is acceptable as a labeling agent for the hemoglobin carrier. Because of the properties of blood as a medium, protons are not a preferred labeling agent. If insufficient imaging agent attaches to the hemoglobin carrier, a chelating agent such as diethylenetriaminopentaacetic acid may be chemically coupled to hemoglobin for binding an NMR responsive imaging agent. For positron emission tomography, one may incorporate carbon-11 or other suitable atoms directly into a chain of hemoglobin as it is synthesized or one may bind the appropriate chemical to hemoglobin.

The imaging agents according to the invention may be used for visualizing any tissue, including static imaging of tumors, blood vessel patency or dynamic cardiac or brain scanning. Unlike other carriers used in the past, hemoglobin naturally is retained in the bloodstream, potentially leading to a sharper image.

The foregoing description of the specific embodiments reveal the general nature of the invention so that others can, by applying current knowledge, readily modify and/or adapt for various applications such specific embodiments without departing from the generic concept, and, therefore, such adaptations and modifications should and, are intended to be comprehended within the meaning and range of equivalents of the disclosed embodiments. It is to be understood that the phraseology or terminology employed herein is for the purpose of description and not of limitation.

All references and patent applications mentioned in this application are incorporated by reference.

EXAMPLE 1

Angiotensin II is a naturally occurring, short-lived (3–4 mins.) but potent vasoconstrictor peptide. Therapeutic applications of this peptide have not been previously explored due to its short half-life in vivo, although use of this peptide in the clinical setting may have significant advantages over current therapeutic approaches where vasoconstrictors are indicated. For example, epinephrine, a commonly used vasoconstrictor, acts both on systemic blood pressure and on heart rate, which may induce negative side effect. However, angiotensin II acts only on vasal tone, and thus can be utilized in situations where only blood pressure must be increased without the additional physiological burden of increased cardiac rhythym.

Angiotensin II is a linear octapeptide (DRVYIHPF-COO-) (SEQ ID NO:20). The initial concern was the synthesis of an analogue with suitable potency that is also appropriate for delivery with hemoglobin. Eight different peptides were synthesized using standard boc-benzyl procedures, and purified by C4 reverse phase chromatography. Several different modifications of the N terminus, C terminus, or body of the peptide were made to determine the effect of addition of a cys residue in potency. In the analogue of choice, the amino terminal was modified by added an N-acetyl cysteine (to provide the thiol bond) followed by a glycine (for a more flexible linkage to the native drug moiety). Moreover, a Arg2→Lys mutation was introduced into the native drug moiety to avoid clearance by secondary receptors of angiotensin II. Dose response curves were collected for each analog in rats. The analog of choice resulted in only a 10 fold reduction in vasoconstrictive effect, and was therefore suitable for further use.

A hemoglobin mutant (alpha D75C) of a known pseudotetramer, SGE1.1, described in Hoffman, et al., WO88/09179, was expressed and purified using techniques known to a person skilled in the art. SGE1.1 is composed of a di-alpha globin (des-Val-alpha globin joined by a glycine to a normal alpha globin), and two beta globins with the Presbyterian (beta108 Asn→Lys) mutation. The mutation D75C (i.e., of a surface aspartic acid to a cysteine) -allows for the formation of a disulfide bond with the peptide of interest. The region around the mutation is a charge neutral, sterically open region and would thus be relatively susceptible to attack by endogenous serum reducing agents. A single angiotensin II molecule was coupled to each hemoglobin molecule (1 peptide drug:1 pseudotetramer), and half-life data was obtained in rats. The hemoglobin-analog conjugate had a half-life that was significantly enhanced over the free analog (overall delivery time of ca. 60 minutes of the analog-conjugate, vs. ca. 1.25 minutes for the free angiotensin II analog, both measured in rats). Moreover, administration of the reductant dithiothreitol after decay of the analog-conjugate response (e.g. a return of blood pressure to baseline levels) resulted in an increase of the blood pressure and a more prolonged release. This suggest that reduction of the peptide-hemoglobin disulfide bond is the mechanism of release of the drug from the carrier. Note that all data were collected with the concomitant adminstration of atropine to avoid tachyphylaxis and/or bradycardia.

EXAMPLE II

The same set of experiments were performed as outlined above, but using a different hemoglobin mutant. The second hemoglobin mutant chosen was another surface alpha chain mutant, alpha Lys 16 Cys. In contrast to the hemoglobin mutant described in example one, the lysine that is replaced by cysteine is located 3.56 Å from a carboxylate in the oxy structure and 3.8 Å away in the deoxy, resulting in placement of the Cys in a negatively charged environment. The half-life of this hemoglobin-analog conjugate was 200 minutes, versus the 60 minutes determined above. Moreover, administration of a bolus of dithiothreitol did not result in significantly enhanced or prolonged delivery, suggesting that the charged environment in the local area of the disulfide bond between the analog and the hemoglobin alpha chain inhibited attack by endogenous serum reductants.

EXAMPLE 3

We have also prepared a cyclic analog of atrial natriuretic factor (ANF), and conjugated it to a cysteine-substituted hemoglobin. Rat ANF is a 28mer peptide hormone with the sequence. ANF is released by atrial cells in the heart in response to an increase in atrial stretching. It regulates electrolyte balance in the blood by its natriuretic and diuretic effects, and causes relaxation of smooth muscle. In the casclature, this leads to a relaxation of blood vessels and an increase in blood pressure. The serum half life of free ANF is 1–2 mins., and is mediated by cleavage of the hormone into inactive fragments by atrial peptidase, in the renal tubules, and by binding to clearance receptors. The free analogue has a similar serum half-life.

The amino acid sequences of wild type ANF and the ANF analogue are shown below.

(SEQ ID NO:21)
wtANF -SLRRSSC-FGGRIDRIGAQSGLGCNSFRY

ANF' C----SS<u>K</u>GFGGRIDRI------<u>D</u>--FR-amide   (SEQ ID NO:22)

The boldfaced cysteines, (C) of wtANF are linked by a disulfide bond. The underlined Lysine (K) and Aspartic Acid (D) of ANF' are linked by a lactam (—NHC(=O)—) bond. The cysteine of ANF' is modified to bear N-acetyl and nitropyridine sulfenyl groups. The residues omitted from wtANF are not essential to its activity and their omission simplified synthesis. The N-terminal cysteine is of course provided for crosslinking to the hemoglobin. The lactam ring replaced the original disulfide bridge; the lactam ring will not participate in crosslinking or release. The inserted glycine is intended to increase protease resistance.

The preparation of the ANF analogue began with a solid-phase synthesis of the amino acid sequence indicated. The cysteine was added with the NPys group already attached. The cysteine thiol was protected with boc, the serine hydroxyls with -O-Benzyl, the epsilon amino group of the Lysine with FMOC, the arginines with tos (toluene sulfonyl), the first aspartic acid with cyclomethyl ester, and the second aspartic acid with fluorenyl methyl ester. Pyridine was used to selectively deprotect the Lys-4 and Asp-14. Their side chains were then cyclized using three cycles of addition of HBTU {2-(1H-benzotriazol-1-yl)-1,1,3,3-tetramethyluronium hexafluorophosphate} and hydroxybenzotriazole dissolved in DMF. Trifluoracetic acid was used to remove the N-terminal boc group and the cysteine was N-acetylated with acetic anhydride. The peptide was cleaved from the resin with HF, which incidentally also removed all protecting groups save for NPys. The analogue was purified by C-4 reversed phase HPLC and attached to the D&%C mutant of SGE1.1 by mixing them in a 2:1 peptide:Hb ratio for two hours and then isolating the conjugate by GFC.

When the ANF analogue was disulfide bonded to the D75C mutant of SGE1.1, and the conjugate (119 mg D75C mutant and 2.9 mg ANF analogue; 0.78 moles ANF analogue per mole of Hgb) administered to a male 250 g rat (given a continuous infusion of atropine to prevent brachycardia), mean systemic blood pressure declined slowly over a period of about 100 minutes (maximum decrease=32 mmg), with the drop first becoming significant at about 30 min.

What is claimed:

1. A diagnostic reagent comprising a hemoglobin-like protein conjugated to or incorporating a tracer, wherein the tracer is covalently bound, directly or indirectly, to a cysteine residue of the hemoglobin-like protein, and the cysteine residue corresponds to a residue which in the corresponding normal human globin subunit, is not a cysteine residue.

2. The reagent of claim 1 wherein said tracer contains a radioactive isotope.

3. The reagent of claim 1 wherein said tracer contains an isotope responsive to nuclear magnetic resonance.

4. A diagnostic imaging method comprising:
administering the reagent of claim 2 to an individual; and measuring the radiation emitted.

5. A diagnostic imaging method comprising:
administering the reagent of claim 3 to an individual; and imaging the individual for a magnetic responsive isotope.

6. A diagnostic reagent comprising a hemoglobin-like protein conjugated to or incorporating a tracer, wherein the tracer is covalently bound, directly or in indirectly, to cysteine residue of the hemoglobin-like protein, and the cysteine residue corresponds to a residue which, in the corresponding normal human globin subunit, is not a cysteine residue, and in which the hemoglobin-like protein is a pseudotetramer.

7. A diagnostic imaging method comprising: administering the reagent of claim 1 to an individual and detecting said tracer in vivo.

8. The diagnostic imaging method of claim 1 in which the hemoglobin-like protein is a pseudotetramer.

9. The diagnostic imaging method of claim 5 in which a chelating agent is conjugated to the hemoglobin-like protein and chelates the magnetic responsive epitope.

10. The diagnostic imaging method of claim 1 in which a tumor is imaged.

11. The diagnostic imaging method of claim 1 in which the blood vessels are imaged.

12. The diagnostic imaging method of claim 1 in which the heart or brain are imaged.

13. The method of claim 12 in which the imaging is dynamic.

14. The diagnostic imaging method of claim 4 in which the tracer is technetium-99m.

15. The method of claim 7 in which the tracer is detected by its position emissions.

16. A diagnostic imaging method of claim 7 in which the tracer is carbon-11.

17. A diagnostic reagent comprising a hemoglobin-like protein conjugated or incorporating a tracer, detectable by its position emissions, where the tracer is carbon-11.

18. A diagnostic imaging method comprising: administering the reagent of claim 17 to an individual and detecting said tracer in vivo.

* * * * *

UNITED STATES PATENT AND TRADEMARK OFFICE
CERTIFICATE OF CORRECTION

PATENT NO. : 5,759,517
DATED : June 2, 1998
INVENTOR(S) : David C. Anderson et al.

It is certified that error appears in the above-identified patent and that said Letters Patent is hereby corrected as shown below:

<u>Column 38,</u>
Line 59, "or in indirectly" should read -- or indirectly --.
Lines 60-61, "to cysteine" should read -- to a cysteine --.

Signed and Sealed this

Twenty-fourth Day of July, 2001

Attest:

NICHOLAS P. GODICI
Attesting Officer     Acting Director of the United States Patent and Trademark Office

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Arg Gly Asp Trp
1

( 2 ) INFORMATION FOR SEQ ID NO:2:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=Modified-site
/ note= "Arg(1) is Ac-Arg."

( i x ) FEATURE:
( A ) NAME/KEY: Modified-site
( B ) LOCATION: 4
( D ) OTHER INFORMATION: /label=Modified-site
/ note= "Tyr(4) is Tyr-Me-amide."

( x i ) SEQUENCE DESCRIPTION: SEQ ID NO:2:

Arg Gly Asp Tyr
1

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Modified-site
            / note= "Tyr is N-succinyl-Tyr."

( i x ) FEATURE:
        ( A ) NAME/KEY: Modified-site
        ( B ) LOCATION: 11
        ( D ) OTHER INFORMATION: /label=Modified-site
            / note= "Xaa(11) is D-Glu."

( i x ) FEATURE:
        ( A ) NAME/KEY: Modified-site
        ( B ) LOCATION: 10
        ( D ) OTHER INFORMATION: /label=Modified-site
            / note= "Ala(10) is cyclohexylalanine."

( x i ) SEQUENCE DESCRIPTION: SEQ ID NO:3:

Tyr Glu Pro Ile Pro Glu Glu Ala Ala Ala Xaa
1                5                         10

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Modified-site
            / note= "Cys is Ac-Cys."

( i x ) FEATURE:
        ( A ) NAME/KEY: Modified-site
        ( B ) LOCATION: 4
        ( D ) OTHER INFORMATION: /label=Modified-site
            / note= "Asp is Asp-penicillamine"

( x i ) SEQUENCE DESCRIPTION: SEQ ID NO:4:

Cys Arg Gly Asp
1

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site (B) LOCATION: 1
(D) OTHER INFORMATION: /label=Modified-site
/ note= "His(1) is N-Pr-His."

(ix) FEATURE:
(A) NAME/KEY: Modified-site
(B) LOCATION: 4
(D) OTHER INFORMATION: /label=Modified-site
/ note= "Xaa(4) is D-Val."

(ix) FEATURE:
(A) NAME/KEY: Modified-site
(B) LOCATION: 6..7
(D) OTHER INFORMATION: /label=Modified-site
/ note= "CH2 is between His(6) and Leu(7)."

(ix) FEATURE:
(A) NAME/KEY: Modified-site
(B) LOCATION: 7
(D) OTHER INFORMATION: /label=Modified-site
/ note= "Leu(7) is Leu-OMe."

(xi) SEQUENCE DESCRIPTION: SEQ ID NO:5:

His Trp Ala Xaa Ala His Leu
1               5

(2) INFORMATION FOR SEQ ID NO:6:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Modified-site
/ note= "Xaa(1) is D-p-Cl-Phe."

(ix) FEATURE:
(A) NAME/KEY: Modified-site
(B) LOCATION: 8
(D) OTHER INFORMATION: /label=Modified-site
/ note= "Leu(8) is beta-Leu."

(ix) FEATURE:
(A) NAME/KEY: Modified-site
(B) LOCATION: 9
(D) OTHER INFORMATION: /label=Modified-site
/ note= "Met(9) is Met-amide"

(xi) SEQUENCE DESCRIPTION: SEQ ID NO:6:

Xaa Gln Trp Ala Val Gly His Leu Met
1               5

(2) INFORMATION FOR SEQ ID NO:7:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: peptide
(B) LOCATION: 1
(D) OTHER INFORMATION: /label=Modified-site
/ note= "Xaa(1) is D-Phe as Phe substitution for
residue 6 of 14-mer bombesin."

(ix) FEATURE:

(A) NAME/KEY: Modified-site
(B) LOCATION: 9
(D) OTHER INFORMATION: /label=Modified-site
/ note= "Met(9) is Met-NH2."

(x i) SEQUENCE DESCRIPTION: SEQ ID NO:7:

Xaa Gln Trp Ala Val Gly His Leu Met
1               5

(2) INFORMATION FOR SEQ ID NO:8:

(i) SEQUENCE CHARACTERISTICS:
(A) LENGTH: 9 amino acids
(B) TYPE: amino acid
(C) STRANDEDNESS: single
(D) TOPOLOGY: linear (i i) MOLECULE TYPE: peptide (i x) FEATURE:
(A) NAME/KEY: peptide
(B) LOCATION: 1
(D) OTHER INFORMATION: /label=Modified-site
/ note= "Xaa(1) is a D-Phe as a Phe substitution
for residue 6 of 14-mer bombesin."

(i x) FEATURE:
(A) NAME/KEY: Modified-site
(B) LOCATION: 9
(D) OTHER INFORMATION: /label=Modified-site
/ note= "Met(9) is modified with OMe
as Met- OMe."

(x i) SEQUENCE DESCRIPTION: SEQ ID NO:8:

Xaa Gln Trp Ala Val Gly His Leu Met
1               5

(2) INFORMATION FOR SEQ ID NO:9:

(i) SEQUENCE CHARACTERISTICS:
(A) LENGTH: 5 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:9:

Gly Arg Gly Asp Ser
1               5

(2) INFORMATION FOR SEQ ID NO:10:

(i) SEQUENCE CHARACTERISTICS:
(A) LENGTH: 5 amino acids
(B) TYPE: amino acid
(C) STRANDEDNESS: single
(D) TOPOLOGY: linear (i i) MOLECULE TYPE: peptide (i x) FEATURE:
(A) NAME/KEY: Modified-site
(B) LOCATION: 1
(D) OTHER INFORMATION: /label=Modified-site
/ note= "Phe(1) is p-NH2-Phe."

(i x) FEATURE:
(A) NAME/KEY: Modified-site
(B) LOCATION: 5
(D) OTHER INFORMATION: /label=Modified-site
/ note= "Arg(5) is Arg-amide."

(x i) SEQUENCE DESCRIPTION: SEQ ID NO:10:

```
        Phe  Ile  Gly  Ser  Arg
        1                   5
```

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Modified-site
            / note= "His(1) is Boc-His."

( i x ) FEATURE:
        ( A ) NAME/KEY: Modified-site
        ( B ) LOCATION: 5..6
        ( D ) OTHER INFORMATION: /label=Modified-site
            / note= "CH(OH)-CH2 replaces the peptide
            bond between Leu(5) and Val(6)."

( x i ) SEQUENCE DESCRIPTION: SEQ ID NO:11:

```
    His  Pro  Phe  His  Leu  Val  Ile  His
    1                   5
```

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label=Modified-site
            / note= "Xaa(2) is a D-Trp."

( i x ) FEATURE:
        ( A ) NAME/KEY: Modified-site
        ( B ) LOCATION: 5
        ( D ) OTHER INFORMATION: /label=Modified-site
            / note= "Xaa(5) is a D-Phe."

( i x ) FEATURE:
        ( A ) NAME/KEY: Modified-site
        ( B ) LOCATION: 6
        ( D ) OTHER INFORMATION: /label=Modified-site
            / note= "Lys(6) is Lys-amide."

( x i ) SEQUENCE DESCRIPTION: SEQ ID NO:12:

```
    His  Xaa  Ala  Trp  Xaa  Lys
    1                   5
```

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site (B) LOCATION: 2
(D) OTHER INFORMATION: /label=Modified-site
/ note= "Tyr(2) has an O-sulfonate group."

(ix) FEATURE:
(A) NAME/KEY: Modified-site
(B) LOCATION: 8
(D) OTHER INFORMATION: /label=Modified-site
/ note= "Phe(8) is Phe-amide."

(xi) SEQUENCE DESCRIPTION: SEQ ID NO:13:

Asp Tyr Met Gly Trp Met Asp Phe
1               5

(2) INFORMATION FOR SEQ ID NO:14:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 2
(D) OTHER INFORMATION: /label=Modified-site
/ note= "Tyr(2) is Tyr-O-sulfonate"

(ix) FEATURE:
(A) NAME/KEY: Modified-site
(B) LOCATION: 3
(D) OTHER INFORMATION: /label=Modified-site
/ note= "Xaa(3) is Nle."

(ix) FEATURE:
(A) NAME/KEY: Modified-site
(B) LOCATION: 6
(D) OTHER INFORMATION: /label=Modified-site
/ note= "Xaa(7) is Nle."

(ix) FEATURE:
(A) NAME/KEY: Modified-site
(B) LOCATION: 8
(D) OTHER INFORMATION: /label=Modified-site
/ note= "Phe(8) is Phe-amide."

(xi) SEQUENCE DESCRIPTION: SEQ ID NO:14:

Asp Tyr Xaa Gly Trp Xaa Asp Phe
1               5

(2) INFORMATION FOR SEQ ID NO:15:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Modified-site
/ note= "Xaa(1) is NAc-(D)Tyr-O-sulfonate."

(ix) FEATURE:
(A) NAME/KEY: Modified-site
(B) LOCATION: 7
(D) OTHER INFORMATION: /label=Modified-site
/ note= "Phe(7) is Phe-amide"

(xi) SEQUENCE DESCRIPTION: SEQ ID NO:15:

```
Xaa  Met  Gly  Trp  Met  Asp  Phe
1              5
```

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Asp  Pro  Asp  Pro  Glu
1              5
```

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label=Modified-site
            / note= "Xaa(2) is D-Ala."

( x i ) SEQUENCE DESCRIPTION: SEQ ID NO:17:

```
Tyr  Xaa  Phe  Asp  Val  Val  Gly
1              5
```

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label=Modified-site
            / note= "Xaa(2) is D-Ala."

( x i ) SEQUENCE DESCRIPTION: SEQ ID NO:18:

```
Tyr  Xaa  Phe  Glu  Val  Val  Gly
1              5
```

( 2 ) INFORMATION FOR SEQ ID NO:19:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /label=Modified-site
            / note= "Xaa(2) is D-Arg."

-continued ( i x ) FEATURE:
    ( A ) NAME/KEY: Modified-site
    ( B ) LOCATION: 4
    ( D ) OTHER INFORMATION: /label=Modified-site
       / note= "Lys(4) is Lys-amide."

( x i ) SEQUENCE DESCRIPTION: SEQ ID NO:19:

```
Tyr  Xaa  Phe  Lys
1
```

( 2 ) INFORMATION FOR SEQ ID NO:20:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Asp  Arg  Val  Tyr  Ile  His  Pro  Phe
1                     5
```

( 2 ) INFORMATION FOR SEQ ID NO:21:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
Ser  Leu  Arg  Arg  Ser  Ser  Cys  Phe  Gly  Gly  Arg  Ile  Asp  Arg  Ile  Gly
1                     5                         10                          15
Ala  Gln  Ser  Gly  Leu  Gly  Cys  Asn  Ser  Phe  Arg  Tyr
                20                         25
```

( 2 ) INFORMATION FOR SEQ ID NO:22:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Cys  Ser  Ser  Lys  Gly  Phe  Gly  Gly  Arg  Ile  Asp  Arg  Ile  Asp  Phe  Arg
1                     5                         10                          15
```